(12) United States Patent
Guichard et al.

(10) Patent No.: US 7,741,280 B2
(45) Date of Patent: Jun. 22, 2010

(54) MULTIMERIC MOLECULES, THE PREPARATION METHOD THEREOF AND USE OF SAME FOR THE PREPARATION OF MEDICAMENTS

(75) Inventors: Gilles François Roger Guichard, Wolfisheim (FR); Sylvie Victorine Lucienne Fournel, Strasbourg (FR); Alberto Bianco, Strasbourg (FR); Johan Félicien Heobeke, Schiltigheim (FR); Sylviane Muller, Strasbourg (FR)

(73) Assignee: Centre National de la Recherche Scientifique, Paris (FR)

( * ) Notice: Subject to any disclaimer, the term of this patent is extended or adjusted under 35 U.S.C. 154(b) by 1274 days.

(21) Appl. No.: 10/516,083

(22) PCT Filed: May 28, 2003

(86) PCT No.: PCT/FR03/01613

§ 371 (c)(1), (2), (4) Date: Jul. 25, 2005

(87) PCT Pub. No.: WO03/102207

PCT Pub. Date: Dec. 11, 2003

(65) Prior Publication Data

US 2006/0035839 A1 Feb. 16, 2006

(30) Foreign Application Priority Data

May 30, 2002 (FR) .................................. 02 06631

(51) Int. Cl.
*A61K 38/12* (2006.01)
(52) U.S. Cl. ........................................... 514/9; 530/317
(58) Field of Classification Search ....................... None
See application file for complete search history.

(56) References Cited

FOREIGN PATENT DOCUMENTS

| WO | WO 99/52877 | 10/1999 |
|---|---|---|
| WO | WO 01/42298 | 6/2001 |
| WO | WO 01/49866 | 7/2001 |
| WO | WO 02/00893 | 1/2002 |

OTHER PUBLICATIONS

Vaccine Development and Testing, accessed at http://www.hhs.gov/nvpo/factsheets/fs_tableII_doc1.htm, 4 pages, last updated Aug. 2001.*
M. Habib et al. J. Immunol. (2007) 178(11), pp. 6700-6704.*
G Aversa et al.: "CD40 ligand-CD40 interaction in Ig isotype switching in mature and immature human B cells" Seminars in Immunology., vol. 6, 1994, pp. 295-301, XP002237774 W.B. Saunders Company, PA., US ISSN: 1044-5323 the whole document.
L E Haswell et al.: "Analysis of the oligomeric requirements for signaling by CD40 using soluble multimeric forms of its ligans, CD154" European Journal of Immunology vol. 31, No. 10, Oct. 2001, pp. 3094-3100, XP002237771 Weinheim, DE ISSN: 0014-2980.
Y-M Hsu et al.: "Heteromultimeric complexes of CD40 ligand are present on the cell surface of human T lymphocytes" Journal of Biological Chemistry., vol. 272, No. 2, 1997, pp. 911-915, XP002237772 American Society of Biological Chemists, Baltimore, MD., US ISSN: 0021-9258.
Archives of Biochemistry and Biophysics, vol. 392, No. 2, Aug. 15, 2001, pp. 208-218, XP002237773 New York, US, US ISSN: 0003-9861.

* cited by examiner

*Primary Examiner*—Andrew D Kosar
(74) *Attorney, Agent, or Firm*—Young & Thompson

(57) ABSTRACT

The invention relates to a multimeric molecule which can imitate a natural multimeric proteinaceous ligand. The invention also relates to a multimeric molecule as defined above which is characterised in that it has the following general formula: $A\text{-}X_n$, wherein: n is equal to 3, 4, 5 or 6; A denotes a chemical group which is functionalised by at least three amine functions or COOH functions; and X denotes a D, B-D or B(D)-D' group, in which B is a spacer and D and D' are peptides or pseudopeptides corresponding to a sequence which is derived from the ligand and selected from residual matter forming the interface with the receptor and which can interact with the receptor.

17 Claims, 12 Drawing Sheets

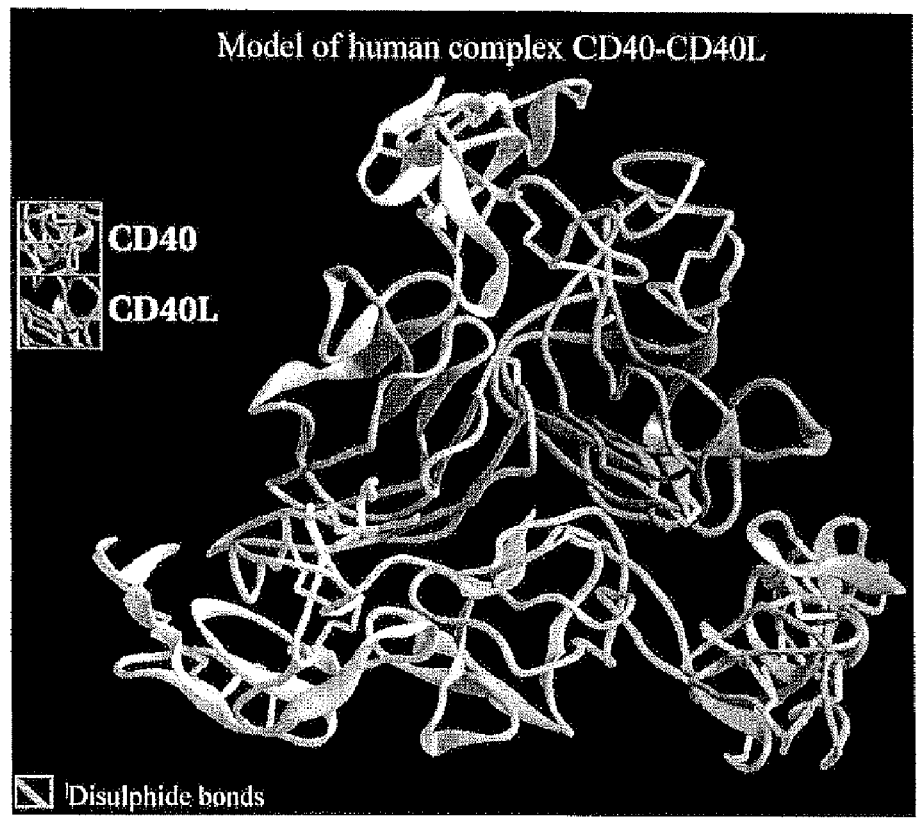
FIGURE 1A
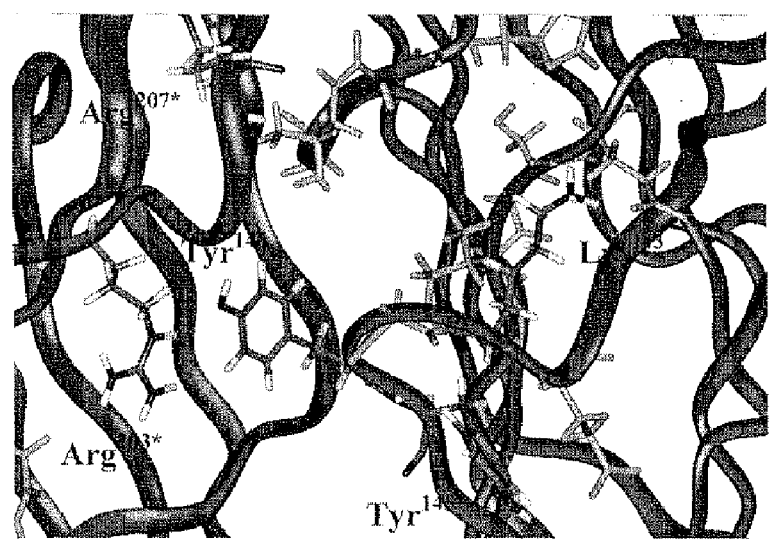

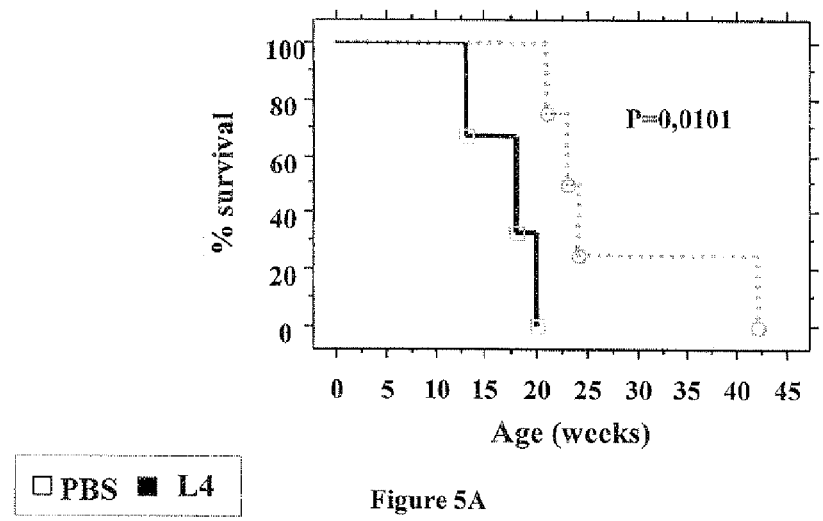
Figure 5A
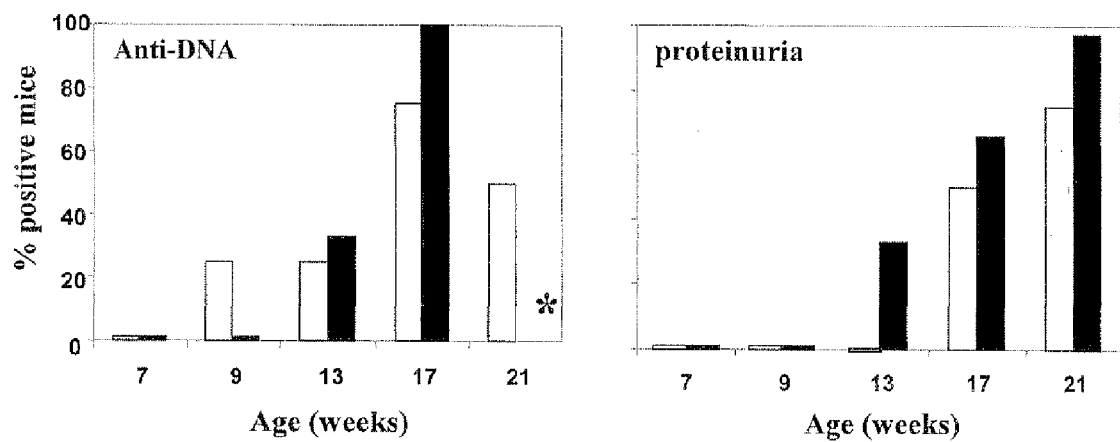
Figure 5B
Figure 5C a) Fmoc-6-aminocaproic acid, DIEA, DCM; b) 25% piperidine/DMF;
c) Fmoc-Xaa-OH BOP, HoBt, DIEA, DMF; d) 1,1,1,3,3,3-hexafluoro-2-propanol/ DCM (60/40)

a) EtOCOCl, NMM, THF; b) CH$_2$N$_2$/Et$_2$O; c) CF$_3$COOAg, NMM, THF/10% H$_2$O
d) iodomethane, K$_2$CO$_3$, acetonitrile

MULTIMERIC MOLECULES, THE PREPARATION METHOD THEREOF AND USE OF SAME FOR THE PREPARATION OF MEDICAMENTS

A subject of the invention is novel multimeric molecules, their preparation process, as well as their use for the preparation of medicaments.

A subject of the invention is also molecules capable of activating or inhibiting the immune response.

The importance of the CD40/CD40L couple in the immune response has led numerous groups to use antibodies directed against these two molecules for therapeutic purposes, in order to inhibit or activate the immune system. The administration of anti-CD40L antibodies has produced encouraging results in the treatment of auto-immune diseases such as murine experimental allergic encephalomyelitis (a model of human multiple sclerosis) (Howard et al., 1999) or in the treatment of rejection of renal allografts in monkeys (Kirk et al., 1999). In these two cases, the antibodies have inhibited harmful activity of the immune system. Conversely, the use of agonist anti-CD40 antibodies has made it possible on the one hand, to strongly increase the response to peptidic anti-tumour vaccines in mice (Diehl et al., 1999) and on the other hand, to increase the effectiveness of the $CD4^+T$ cells in combating murine tumours (Sotomayor et al., 1999; Lode et al., 2000). Tumour regression in murine models was detected after injection of dendritic cells (DCs) transformed by an adenovirus encoding CD40L (Kikuchi et al., 2000). Finally, activation of the dendritic cells by the interaction of their CD40 molecule with CD40L is capable of protecting mice from infection by a parasite, *Trypanosoma Cruzi* (Chaussabel et al., 1999). In all these works, the particular valency of the CD40L molecule, which combines in the form of a trimer in order to form, with CD40, hexavalent complexes, makes it difficult to produce functional antibodies capable of interfering with the functions of the CD40/CD40L couple. The development of the adenovirus coding for CD40L is a partial response to this drawback. However, their use is not without problems in humans. Finally, the particular valency of the system makes it difficult to discover synthesis molecules capable of interfering with the CD40/CD40L interaction.

A purpose of the invention is to provide multimeric ligands designed to interfere in protein-protein interactions.

A purpose of the present invention is also the preparation of molecules capable of interfering with protein-protein multivalent interactions.

A purpose of the present invention is also the preparation of molecules capable of modulating the activity of members of the TNF and TNF-R families.

A purpose of the invention is to provide a synthesis molecule acting on the CD40/CD40L system.

A purpose of the present invention is also to provide molecules capable of acting as adjuvants or immunosuppressors.

The present invention relates to a multimeric molecule capable of mimicking, with an agonist or antagonist activity, a natural protein multimeric ligand.

The present invention also relates to a multimeric molecule capable of producing effects different from those produced by the natural multimeric ligand belonging to the TNF family, capable of being beneficial in a pathology.

By "molecule capable of mimicking a ligand with an agonist activity", is meant a molecule capable of reproducing some or all of the functions of the natural ligand.

By "molecule capable of mimicking a ligand with an antagonist activity", is meant a molecule capable of inhibiting some or all of the functions of the natural ligand.

By "natural protein multimeric ligand", is meant any protein active on its receptor in multimeric form, namely homo-dimeric, homo-trimeric, homo-tetrameric or homo-oligo-meric, by non-covalent self-assembly.

The present invention relates to a multimeric molecule as defined above, capable of mimicking a receptor ligand of the TNF superfamily.

The "TNF superfamily" designates a family of molecules having structural or functional characteristics similar to those of TNF, these molecules being essentially involved in the immune response.

According to an advantageous embodiment of the invention, the multimeric molecule of the invention is characterized in that the ligand is a ligand of the CD40 molecule.

The CD40 molecule is a 48 kDa transmembrane molecule which belongs to the "TNF receptors" superfamily. It is constitutively expressed by the antigen-presenting cells such as the dendritic cells, the monocytes and the B lymphocytes. It interacts trivalently with CD40L (CD154) expressed on the activated T cells, the leucocytes (monocytes/macrophages, NK cells, basophiles, eosinophiles), the activated platelets as well as on non-haematopoietic cells (smooth muscle cells, epithelial cells, endothelial cells). At the surface of these different cells, its expression is inducible and persistent, unlike its expression on the activated T cells which is only transitory. The CD40/CD40L interaction is central in the development and control of the humoral and cellular immune responses.

The present invention relates to a multimeric molecule as defined above, characterized in that it corresponds to the following general formula:

$$A\text{-}X_n$$

in which:

n is equal to 3, 4, 5 or 6,

A is a chemical group, functionalized by at least three amine functions or COOH functions, X represents a -D, —B-D or —B(D)-D' group, in which:
  B is a spacer arm,
  -D and -D' are peptides or pseudopeptides corresponding to a sequence derived from the ligand, chosen from the residues forming the interface with the ligand receptor, which sequence is capable of interacting with the receptor.

The chemical group A is a chemical group functionalized so that it allows the bond with the group X. A is also called "core molecule".

By "core molecule" is meant a chemical group having a central role in the presentation of the n X groups in the multimeric molecule.

By "spacer arm", is meant an organic chain used to move the D group to the desired distance from A.

By "peptides or pseudopeptides", is meant a sequence of residues of natural or non-natural amino acids, interconnected by amide bonds. A pseudopeptide is obtained by replacement of one or more amide bonds in the peptide by a chemical bond different in nature.

By "sequence derived from the ligand, chosen from the residues forming the interface with the ligand receptor", is meant a peptide sequence belonging to the primary sequence of the ligand and the number of amino acids of which is comprised between 3 and 10, and structural studies (X-ray diffraction, nuclear magnetic resonance, molecular modelling, directed mutagenesis) of which have shown that at least one of the amino acids composing it is in non-covalent interaction (hydrogen bond, cation-pi interaction, salt bridge, hydrophobic interaction and van der Waals) with an amino acid residue of the receptor.

The present invention also relates to a multimeric molecule, characterized in that it corresponds to the following general formula:

A-X$_n$ in which:

n is equal to 3, 4, 5 or 6,

A is a chemical group, functionalized by at least three amine functions or COOH functions or SH functions or S-Npys (S-nitro-pyridinesulphenyl) functions or S-Pys (S-pyridinesulphenyl) functions, and is in particular different from a protein, X represents a -D, —B-D or —B(D)-D' group, in which:
B is a spacer arm,
-D and -D' represent peptides or pseudopeptides corresponding to a sequence derived from a ligand, chosen from the residues forming the interface with the ligand receptor, which sequence is capable of interacting with the receptor, said ligand being chosen from the ligands of receptors of the TNF superfamily, and in particular from the following ligands: EDA, CD40L, FasL, OX40L, AITRL, CD30L, VEGI, LIGHT, 4-1BBL, CD27L, LTα, TNF, LTβ, TWEAK, APRIL, BLYS, RANKL and TRAIL.

The present invention also relates to a multimeric molecule, characterized in that it corresponds to the following general formula:

A-X$_n$ in which:

n is equal to 3, 4, 5 or 6,

A is a chemical group, functionalized by at least three amine functions or COOH functions, and is in particular different from a protein, X represents a -D, —B-D or —B(D)-D' group, in which:
B is a spacer arm,
-D and -D' represent peptides or pseudopeptides corresponding to a sequence derived from a ligand, chosen from the residues forming the interface with the ligand receptor, which sequence is capable of interacting with the receptor, said ligand being chosen from the ligands of receptors of the TNF superfamily, and in particular from the following ligands: EDA, CD40L, FasL, OX40L, AITRL, CD30L, VEGI, LIGHT, 4-1BBL, CD27L, LTα, TNF, LTβ, TWEAK, APRIL, BLYS, RANKL and TRAIL.

The expression "-D and -D' corresponding to a sequence derived from a ligand, which sequence is capable of interacting with the receptor" can be defined as follows: the -D and -D' sequences are chosen on the basis of available structural data (X-ray diffraction or molecular modelling and directed mutagenesis) for their involvement in the interaction with the corresponding receptor. Thus in the natural protein, all or part of the residues of these sequences are in interaction (hydrogen bond, hydrophobic bond, H bond, cation-Pi bond, salt bridges, van der Waals interactions) with part of the corresponding receptor or receptors. Nevertheless the isolated peptides -D or -D' can have affinities for the receptor too weak to be measured. The gain in affinity is provided by the multimerization as described in the present invention.

The ligands of the TNF superfamily are chosen from the list provided by Locksley et al. (2001) and are in particular the following:

| Name of the ligand | References |
|---|---|
| EDA | Laurikkala J, Development (2002) May; 129(10): 2541-53 |
| CD40L | J. Singh et al., Protein Science (1998), 7, 1124-1135 |
| FasL | Starling et al., Biochemistry (1998), 37, 3723-3726 |
| OX40L | Weinberg A D., Trends Immunol (2002) Feb; 23(2): 102-9 (review) |
| AITRL | Kwon B et al., J Biol Chem (1999) Mar 5; 274(10): 6056-61 |
| CD30L | Opat S, Gaston J S. Autoimmunity (2000); 33(1): 45-60 (review) |
| VEGI (or TL1) | Migone T S et al., Immunity (2002) Mar; 16(3): 479-92 |
| LIGHT | Wang J et al., J Immunol (2001) Nov 1; 167(9): 5099-105 |
| 4-1BBL | Kwon B, Trends Immunol (2002) Aug; 23(8): 378-80 |
| CD27L | Jacquot S., Immunol Res (2000); 21(1): 23-30 |
| LTα (TNFB) | Banner et al., Cell (1993), 73, 431-445 |
| TNF | Eck et al., J. Biol. Chem. (1989), 264, 17595-17605 |
| Ltβ | Browning J L, Cell (1993) Mar 26; 72(6): 847-56 |
| TWEAK | Chicheportiche Y et al., J Biol Chem (1997) Dec 19; 272(51): 32401-10 |
| APRIL | Yu G et al., Nat Immunol (2000) Sep; 1(3): 252-6 |
| BLYS | Liu Y et al., Cell (2002) Feb 8; 108(3): 383-94 |
| RANKL | Ito S et al., J Biol Chem (2002) Feb 22; 277(8): 6631-6 |
| TRAIL | Mongkolsapaya J et al., Nat Struct Biol (1999) Nov; 6(11): 1048-53 |

According to an advantageous embodiment of the present invention, the molecule of the invention is characterized in that -D and -D' represent peptides derived from the ligand of the human or murine CD40 receptor (CD40L), said peptides belonging to the primary sequence of the CD40L ligand of CD40 and the number of amino acids of which is comprised between 3 and 10.

An advantageous multimeric molecule of the invention is a multimeric molecule characterized in that A has C$_3$ symmetry.

A molecule with C$_3$ symmetry is defined as follows: a molecule belongs to the C$_3$ group if it possesses an axis of the order of 3 (cf. definition in "Physical Chemistry", P W Atkins, Oxford University Press, 1998, p430).

The present invention relates to a multimeric molecule as defined above, characterized in that:
either A is a branched radical with C$_3$ symmetry with the following general formula:

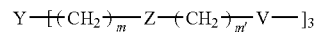

in which:
m and m' are integers comprised from 1 to 5,
V represents an —NH— or —CO— group forming an amide bond with X,
Z represents an oxygen atom or a CH$_2$ group,
Y represents either a nitrogen atom, or an R—C— group or an R—CONH—C— group, in which R can be an alkyl group with 1 to 10 carbon atoms, an alkenyl group with 1 to 10 carbon atoms, an alkynyl group with 1 to 10 carbon atoms, an aryl group with 5 to 12 carbon atoms, an aralkyl group with 5 to 14 carbon atoms or a heteroaryl group with 1 to 10 carbon atoms, said groups are capable of being non-substituted or substituted by 1 to 6 substituents chosen from the —COOH, —NH$_2$, —CONH$_2$ or alkoxy groups,
or A is a cyclic C$_3$ radical corresponding to one of the following general formulae:

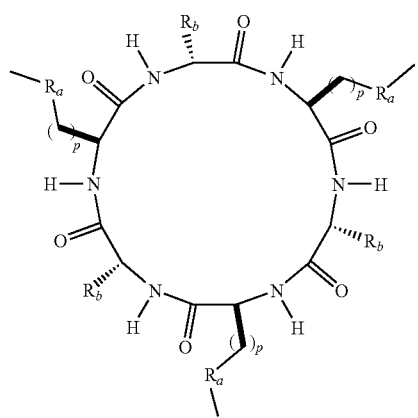
Ia
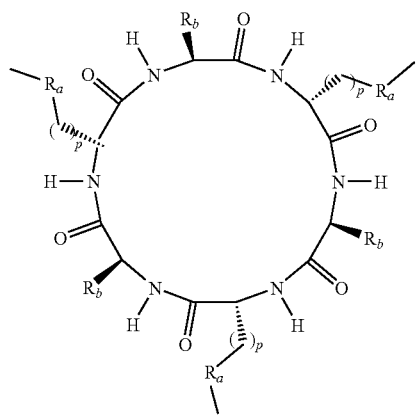
Ib
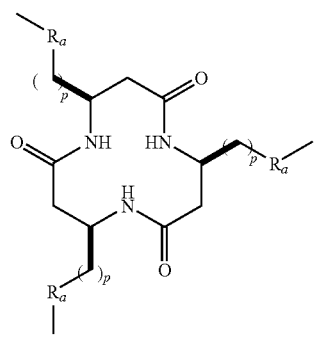
II
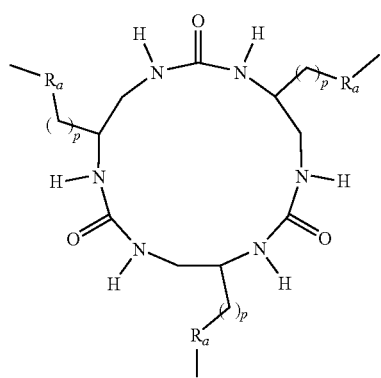
III
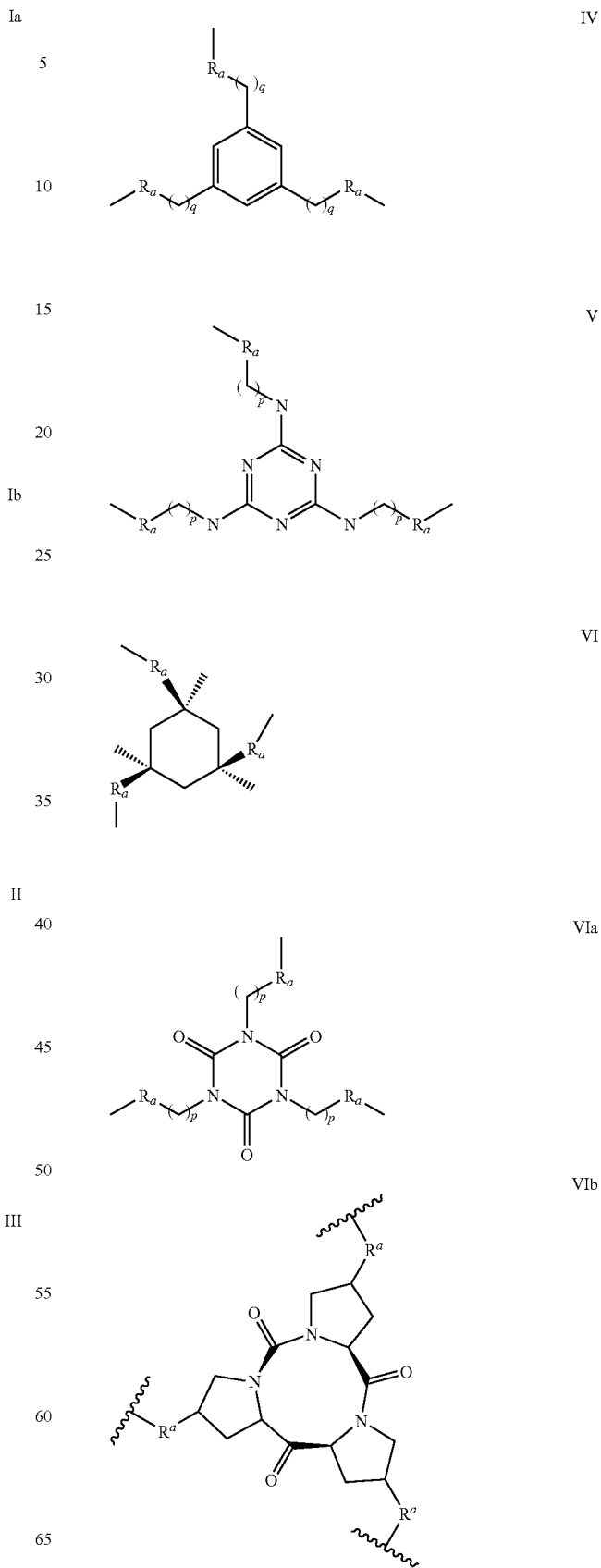

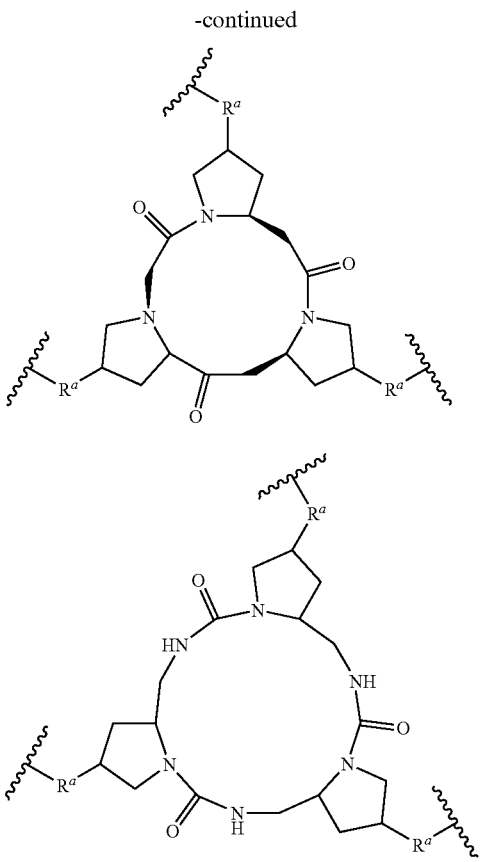

in which:
R$_a$ represents either an —NH— group or a —CO— group forming an amide bond with X,
R$_b$ represents the side chain of a proteinogenic amino acid,
p is an integer comprised from 1 to 4,
q is an integer comprised from 0 to 4,
or A is a non-symmetrical branched radical corresponding to the following general formulae:

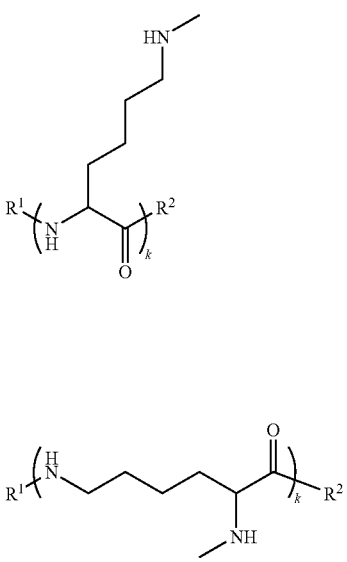

in which:
k represents 3, 4, 5 or 6,
R$^1$ represents either a hydrogen atom, or an amino acid residue chosen from the proteinogenic amino acids, or an RCO—, ROCO— or RNHCO— group, R being as defined above,
R$^2$ represents either an —NH$_2$ group, or an —NHR group, or an amino acid residue chosen from the proteinogenic amino acids, R being as defined above,
B corresponds to one of the following general formulae:

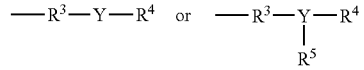

in which:
Y represents a C$_1$-C$_{10}$ alkyl chain or an alkynyl or alkenyl or aryl or aralkyl or heteroaryl group,
R$^3$ represents either an —NH— group when V or R$_a$ is a —CO— group, or a —CO— group when V or R$_a$ is an —NH— group,
R$^4$ and R$^5$ represent independently of one another a —CO— group or an —NH— group,
-D and -D' are peptides or pseudopeptides corresponding to a sequence derived from the ligand which is in interaction with the receptor.

The present invention also relates to a molecule as defined above, characterized in that -D and -D' represent residues derived from the human or murine CD40 receptor ligand (CD40L), chosen from the following:

Lys$^{143}$-Gly-Tyr$^{145}$ (SEQ ID NO: 1), Tyr$^{145}$-Gly-Lys$^{143}$ (SEQ ID NO: 2),
Lys$^{143}$-Gly-Tyr-Tyr$^{146}$ (SEQ ID NO: 3), Tyr$^{146}$-Tyr-Gly-Lys$^{143}$ (SEQ ID NO: 4),
Lys-Pro-Arg (SEQ ID NO: 5), Lys-ψ(CH$_2$NH)Pro-Arg (SEQ ID NO: 24),
Arg$^{200}$-Phe-Glu-Arg-Ile-Leu-Leu-Arg$^{207}$ (SEQ ID NO: 6),
Arg$^{207}$-Leu-Leu-Ile-Arg-Glu-Phe-Arg$^{200}$ (SEQ ID NO: 7),
Arg$^{200}$-Phe-Glu-Arg-Ile$^{204}$ (SEQ ID NO: 25),
Ile$^{204}$-Arg-Glu-Phe-Arg$^{200}$ (SEQ ID NO: 9),
Arg$^{203}$-Ile-Leu-Leu-Arg$^{207}$ (SEQ ID NO: 10),
Arg$^{207}$-Leu-Leu-Ile-Arg$^{203}$ (SEQ ID NO: 11),
Cys$^{218}$-Gly-Gln-Gln-Ser-Ile$^{233}$ (SEQ ID NO: 12),
Ile$^{223}$-Ser-Gln-Gln-Gly-Cys$^{218}$ (SEQ ID NO: 26),
Gly$^{200}$-Ser-Glu-Arg-Ile-Leu-Leu-Lys$^{207}$ (SEQ ID NO: 14),
Lys$^{207}$-Leu-Leu-Ile-Arg-Glu-Ser-Gly$^{200}$ (SEQ ID NO: 15),
Gly$^{200}$-Ser-Glu-Arg-Ile$^{204}$ (SEQ ID NO: 16),
Ile$^{204}$-Arg-Glu-Ser-Gly$^{200}$ (SEQ ID NO: 17),
Arg$^{203}$-Ile-Leu-Leu-Lys$^{207}$ (SEQ ID NO: 18),
Lys$^{207}$-Leu-Leu-Ile-Arg$^{203}$ (SEQ ID NO: 19),
Cys$^{218}$-Glu-Gln-Gln-Ser-Val$^{223}$ (SEQ ID NO: 20),
Val$^{223}$-Ser-Gln-Gln-Glu-Cys$^{218}$ (SEQ ID NO: 21),
or from hybrid peptides constituted by at least two consecutive amino acids of two of the sequences defined above, in particular the peptides of sequences Arg$^{203}$-Ile$^{204}$-Tyr$^{145}$-Tyr$^{146}$ (SEQ ID NO: 22) or Arg$^{203}$-Ile$^{204}$-Tyr$^{146}$-Tyr$^{145}$-Gly$^{144}$-Lys$^{143}$ (SEQ ID NO: 23),
or from fragments of the abovementioned sequences, the amino acids being equally able to be of L or D configuration.

According to an advantageous embodiment of the present invention, the molecule as defined above is characterized in that A corresponds to one of the following formulae:

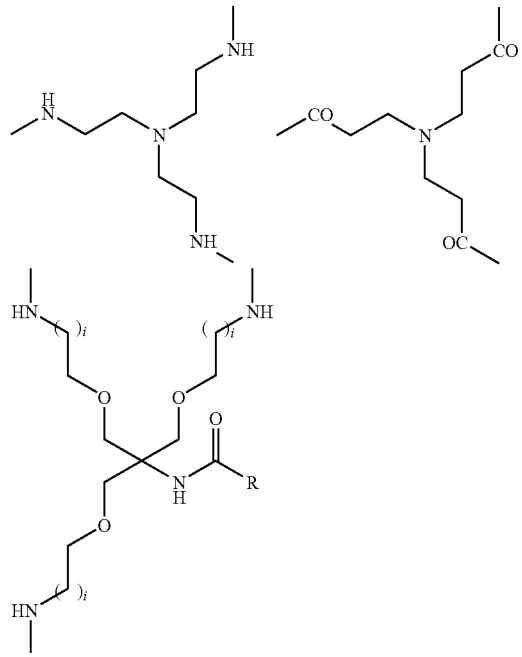

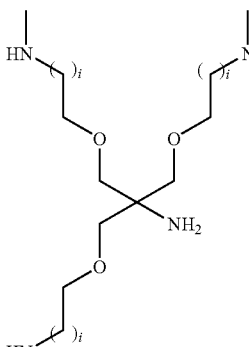

-continued in which i represents an integer greater than or equal to 1.

An advantageous molecule of the present invention is a molecule as defined above, of the following formula (peptide sequences KGYY and YYGK disclosed as SEQ ID NOS 3 and 4, respectively):

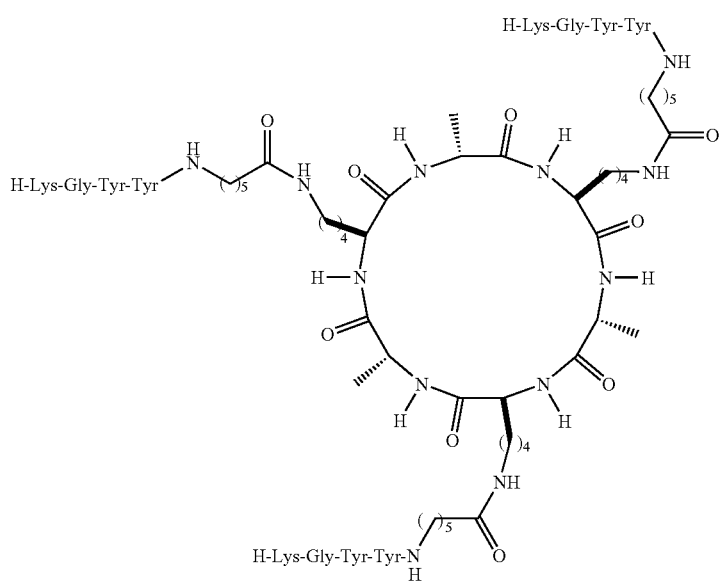

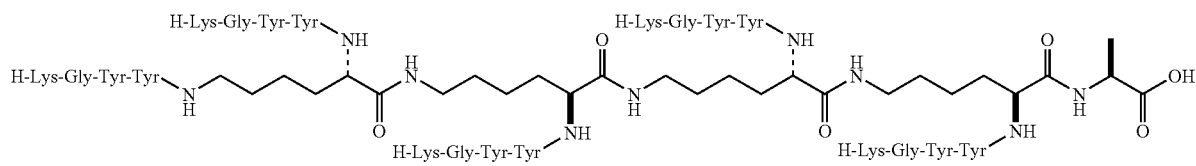

IIa
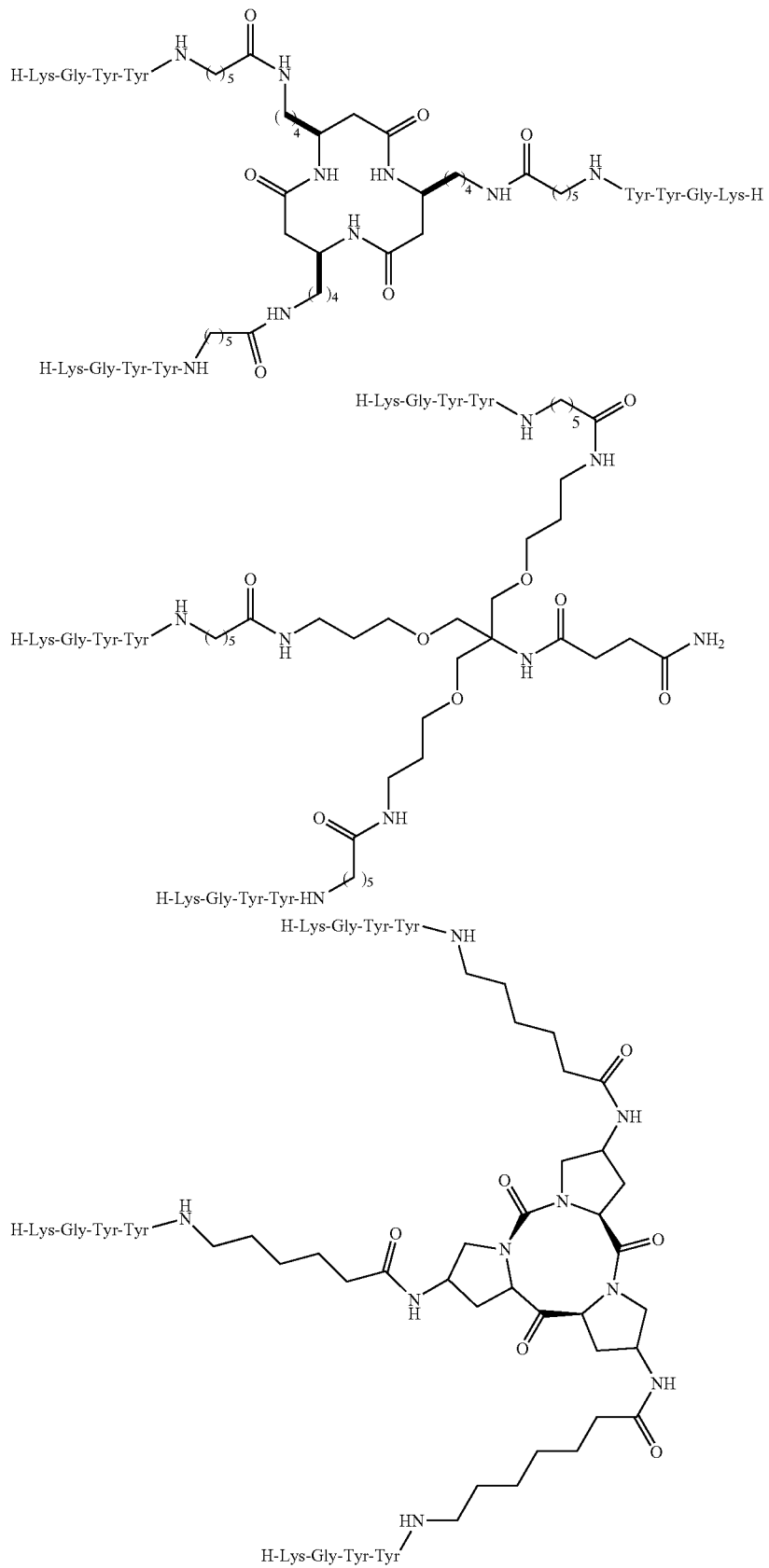

-continued

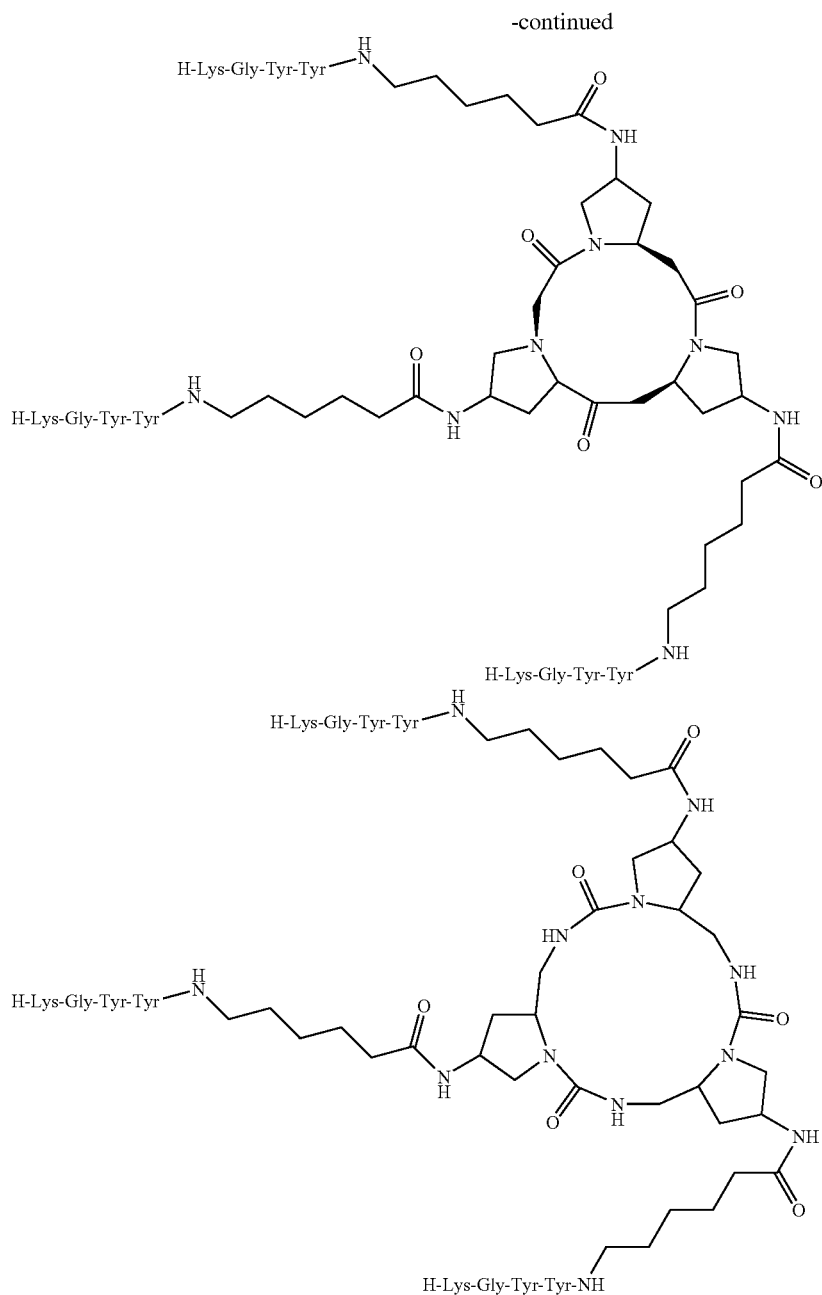

The present invention also relates to a pharmaceutical composition characterized in that it comprises as active ingredient a multimeric molecule as defined above, in combination with a pharmaceutically acceptable vector.

The present invention also relates to a vaccinal composition, characterized in that it comprises as active ingredient a multimeric molecule as defined above, in combination with a pharmaceutically acceptable adjuvant.

The present invention also relates to the use of multimeric molecules as defined above, for the preparation of a medicament intended for the treatment of pathologies involving the inhibition or activation of the immune response.

The immune response must be inhibited during inflammatory diseases (inflammatory rheumatism), auto-immune diseases, hypersensitivity reactions in general and allergies in particular, graft rejections, reactions of the graft against the host.

The immune response must be activated in vaccinations in general, in cancer immunotherapy, in bacterial or viral diseases inducing immunosuppression (measles, AIDS, herpes virus, cytomegalovirus etc.).

The present invention also relates to the use as mentioned above, for the preparation of a medicament intended for the treatment of pathologies involving inhibition of the immune response, such as graft rejections or auto-immune diseases.

Diseases involving inhibition of the immune response include auto-immune diseases such as diabetes, multiple sclerosis, disseminated lupus erythematous or rheumatoid arthritis, graft rejections, in particular within the context of allografts, xenografts or reactions of the graft against the host, as well as hypersensitivity reactions such as allergies, in particular allergic rhinitis and atopic dermatitis, or granulomas.

The compounds according to the present invention, used within the context of inhibition of the immune response, can be administered by intravenous route, by the mucous (oral, airway, nasal, vaginal) routes, by sub-cutaneous, intradermal or epicutaneous route.

The present invention also relates to a pharmaceutical composition, characterized in that it comprises a compound according to the present invention, for the treatment of pathologies involving inhibition of the immune response, which compound is present in the pharmaceutical composition in quantities such that it can be administered at a rate of approximately 100 ng to approximately 5 mg per day and per individual.

The present invention also relates to the use as defined above, for the preparation of a medicament intended for the treatment of pathologies involving the augmentation of the immune response, such as cancers or parasitic, bacterial or viral infections.

Cases involving the activation of the immune response include vaccinations in general, in particular vaccines against influenza or against childhood diseases, cancer immunotherapy, in particular within the context of melanomas or metastatic cancers, or bacterial or viral diseases inducing immunosuppression, in particular within the context of measles, AIDS, herpes virus or cytomegalovirus.

The compounds according to the present invention, used within the context of activation of the immune response, can be administered by intravenous route, by the mucous (oral, airway, nasal, vaginal) routes, by sub-cutaneous, intradermal or epicutaneous route.

The present invention also relates to a pharmaceutical composition, characterized in that it comprises a compound according to the present invention, for the treatment of pathologies involving activation of the immune response, which compound is present in the pharmaceutical composition in quantities such that it can be administered at a rate of approximately 100 ng to approximately 5 mg per day and per individual.

The present invention also relates to the use as defined above, for the preparation of a medicament intended for the treatment of diseases not linked to the immune system, such as lymphomas, atherosclerosis or thrombosis.

The present invention relates to a process for preparation on a solid support of a multimeric molecule as defined above, in which A is a cyclic $C_3$ radical and corresponds to one of formulae Ia, Ib, II, VIb, VIc or VId as defined above, said process being characterized in that it comprises the following stages:
  the formation of a linear precursor of A, which precursor is constituted by an amino acid sequence forming a growing peptide chain, synthesized by successive coupling cycles between residues of N-protected amino acids, three of which carry an $R_a$ group of amine type, and the amine function of the growing peptide chain, and deprotection, the first amino acid residue being attached to a solid support,
  the cyclization of the abovementioned protected linear precursor of A,
  the cleavage of said protective groups, in order to release said protected amine functions,
  the coupling of the three released amine functions with an N-protected spacer arm B,
  the deprotection of the spacer arm B and the coupling of the amine functions released from the spacer arm B, with a D peptide already formed or formed in situ by the sequential assembly of the amino acid residues corresponding to the D peptide, and
  the cleavage of the molecule from the solid support, after the deletion of all the protective groups present on the functionalized side chains of the D peptide, in order to obtain the multimeric molecule according to the invention.

The compounds comprising a cyclic group A having $C_3$ symmetry and corresponding to general formulae Ia, Ib, II, VIb, VIc or VId are obtained by synthesis on a solid support according to the process described hereafter. The group A is first constructed on a solid support by synthesis of its linear precursor and cyclization. Thus, a first amino acid residue, the acid function of which is suitably protected (allyl ester for example), is attached to the support by a reductive amination reaction, by using a resin functionalized by an aldehyde (commercial resins). The linear precursor of A is then assembled by successive coupling cycles (in standard peptide synthesis manner) with an N-protected amino acid (N-Fmoc-Xaa-OH for example, Xaa representing an amino acid or any growing peptide) and deprotection (20% piperidine in DMF for the cleavage of an Fmoc group). The resin washing and filtration techniques, as well as the Fmoc group deprotection techniques are those commonly used in solid phase peptide synthesis. The three amino acids carrying an $R_a$ chain (cf. formulae Ia, Ib or II) are functionalized on their side chain by an amine function which is protected by a protective group orthogonal to the others (TEOC or methyltrityl for example). At the end of the assembly, the last N-protective group is cleaved (in the presence of 20% piperidine in DMF in the case of an Fmoc group) and the protection of the C-terminal ester is cleaved. The linear precursor is then cyclized "head to tail" in the presence of a coupling reagent (standard in peptide synthesis) and a tertiary base such as DIEA or collidine for example. The cyclization reaction can be followed by a colorimetric test such as Kaiser's test (Kaiser et al., 1970). At the end of the cyclization, the protective groups of the amino acids possessing a protected amine function are cleaved and the spacer arm, suitably protected (Fmoc-Ahx (6-amino hexanoic acid)-COOH for example), is coupled in the presence of a coupling agent on the three free amine functions. At the end of this coupling, the protective group of the spacer arm is cleaved and the D peptide is assembled by standard peptide synthesis methods. At the end of the synthesis and once the last protective group is removed, the molecule is cleaved from the resin, for example by treatment with trifluoroacetic acid, lyophilized after precipitation with ether and purified by preparative reversed-phase HPLC on a C18 column for example.

The present invention also relates to a process for the preparation in solution of a multimeric molecule as defined above, in which A is a cyclic $C_3$ radical and corresponds to one of formulae Ia, Ib, II, VIb, VIc or VId as defined above, said process being characterized in that it comprises the following stages:
  the formation of a linear precursor of A, which precursor is constituted by an amino acid sequence forming a growing peptide chain, synthesized by successive coupling cycles between N-protected amino acid residues, three of which carry an amine-type $R_a$ group, and the amine function of the growing peptide chain, and deprotection,
  the cyclization of the abovementioned protected linear precursor of A,
  the cleavage of said protective groups, in order to release said protected amine functions,
  the coupling of the three released amine functions with a -D-B peptide corresponding to a spacer arm B linked to a protected D peptide,
  the deprotection of the protective groups present on the D peptide, in order to obtain the multimeric molecule according to the invention.

The present invention relates to a process for the preparation of a multimeric molecule as defined above, in which A is a branched $C_3$ radical and corresponds to one of formulae IV, V, VI or VIa as defined above, said process being characterized in that it comprises the following stages:

the coupling of the three amine functions of the radical A of formula IV, V, VI or VIa with a protected spacer arm B, the deprotection of the spacer arm B, the assembly of the deprotected spacer arm B with protected amino acids involved in the constitution of a D peptide, by successive cycles of coupling, purification and deprotection of the abovementioned amino acids, the deprotection of the last amino acid involved in the constitution of the D peptide, in order to obtain the multimeric molecule according to the invention.

The compounds of the invention comprising a group A which is a branched radical of $C_3$ symmetry, and corresponding in particular to formulae IV, V, VI or VIa, can be synthesized in solid phase or in solution according to the procedure described in detail hereafter.

When the radical A is functionalized by amine functions, the suitably protected spacer arm (Boc-Ahx-OH for example) is coupled in the presence of a coupling reagent according to peptide synthesis processes on the three amine functions of A. At the end of this coupling, the reaction of which can be monitored by thin layer chromatography, the product is isolated and purified on a silica column according to standard organic synthesis techniques. The Boc group is then cleaved by trifluoroacetic acid, and the D peptide is assembled in solution by successive stages of coupling, purification and deprotection of the Boc group. At the end of the synthesis, the protective groups on the side chains are cleaved by catalytic hydrogenation or by treatment with hydrofluoric (HF) acid. The trimeric molecule is then purified by preparative reversed-phase HPLC on a C18 column for example.

When the radical A is functionalized by carboxylic acid functions, the suitably protected spacer arm (hexamethylene diamine monoprotected by a Boc group for example) is coupled in the presence of a coupling reagent according to peptide synthesis processes on the three carboxylic acid functions of A. At the end of this coupling, the reaction of which can be monitored by thin layer chromatography, the product is isolated and purified on a silica column according to standard organic synthesis techniques. The Boc group is then cleaved by trifluoroacetic acid, and the D peptide is assembled in solution by successive stages of coupling, purification and deprotection of the Boc group. At the end of the synthesis, the protective groups on the side chains are cleaved by catalytic hydrogenation or by treatment with hydrofluoric (HF) acid. The trimeric molecule is then purified by preparative reversed-phase HPLC on a C18 column for example.

The present invention relates to a process for the preparation on a solid support of a multimeric molecule as defined above, in which A is a non-symmetrical branched radical corresponding to one of formulae VII or VIII as defined above, said process being characterized in that it comprises the following stages:

the grafting of a lysine on a solid support, each of the two amine functions of the lysine, in positions α and ε respectively, being protected by different and orthogonal protective groups respectively, the extension of the peptide chain formed from the lysine, to the desired length, by successive couplings and deprotections either of the amine functions in position α only, in order to obtain the radical A of formula VII, with protected amine functions in position E, or of the amine functions in position ε only, in order to obtain the radical A of formula VIII, with protected amine functions in position α, the coupling of the deprotected amine functions in position ε in the radical A of formula VII or in position α in the radical A of formula VIII, with a protected arm B, the assembly of the deprotected spacer arm B with a D peptide already formed or formed in situ by the sequential assembly of the amino acid residues corresponding to the D peptide, and the cleavage of the molecule thus obtained from the solid support, after the deletion of all the protective groups present on the functionalized side chains of the D peptide.

The compounds of the invention comprising a group A which is a non-symmetrical branched radical, can be synthesized in solid phase according to the procedure described in detail hereafter.

An Fmoc-Xaa-Wang resin (Xaa can be any amino acid or growing peptide) or a commercial Fmoc-Rink-amide resin is used. After cleavage of the Fmoc group with 25% piperidine in DMF (dimethylformamide) (2×15 minutes), the amino acid, carrying the functionalized amine chain, suitably protected in orthogonal manner in particular by an Fmoc group or an Mtt (methyltrityl) group in the case of an amine function (Fmoc-Lys(Mtt)-OH for example), is activated with a coupling agent in the presence of a tertiary base and coupled to the resin. The Mtt or Fmoc group is cleaved selectively by treatment with a solution (6 ml) of 85% dichloromethane (DCM), 10% triisopropylsilane (TIS), 5% trifluoroacetic acid (TFA) (3×3 minutes) (in the case of Mtt), or 25% piperidine in DMF (in the case of Fmoc). The chain is extended to the desired length (k being an integer comprised between 3 and 6) by successive couplings and deprotections using the same amino acid (Fmoc-Lys(Mtt)-OH for example). After deprotection of the last Fmoc or Mtt group, the remainder of the protective groups (Mtt or Fmoc) are cleaved and the suitably protected spacer arm (Fmoc-Ahx-COOH for example) is coupled in the presence of a coupling agent on the free amine functions. At the end of this coupling, the protective group of the spacer arm is cleaved and the D peptide is assembled by standard peptide synthesis methods. At the end of the synthesis and once the last protective group has been removed, the peptide is cleaved from the resin (treatment with trifluoroacetic acid for example), lyophilized after precipitation from ether and purified by preparative reversed-phase HPLC on a C18 column for example.

DESCRIPTION OF THE FIGURES

FIG. 1A represents the molecular model of the trivalent CD40-CD40L complex.

FIG. 1B represents CD40L residues situated at the interface and essential to the interaction with CD40. The residues with an asterisk belong to the second CD40L sub-unit forming the interface.

FIG. 3A represents the expression of CD95 when the abovementioned BL41 cells ($5.10^5$/ml) are incubated with non-transfected 3T6 fibroblasts.

FIG. 3B represents the expression of CD95 when the abovementioned BL41 cells ($5.10^5$/ml) are incubated with 3T6 fibroblasts transfected by CD40L.

FIG. 3C represents the expression of CD95 when the abovementioned BL41 cells (5.10⁵/ml) are incubated with non-transfected 3T6 fibroblasts, in the presence of anti-CD40L antibodies.

FIG. 3D represents the expression of CD95 when the abovementioned BL41 cells (5.10⁵/ml) are incubated with 3T6 fibroblasts transfected by CD40L, in the presence of anti-CD40L antibodies.

Tritiated thymidine was added at a concentration of 1 µci/well (0.8.10⁵ cells/well) for the last 8 hours of culture and the incorporation of tritiated thymidine measured using a gaseous scintillation β counter.

Figure 4A:
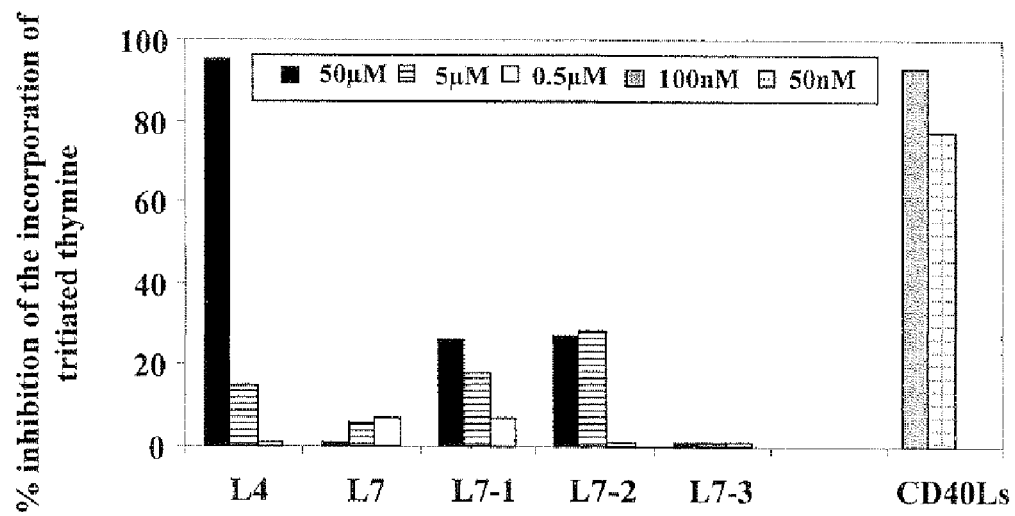
FIG. 4A represents the inhibition of the incorporation of tritiated thymidine of the BL41 Burkitt lymphoma cells (4.10⁵ cells/ml) after culture for 24 hours in the presence of different concentrations of ligands (L4, L7, L7-1, L7-2 or L7-3) or soluble CD40L (sCD40L). The black columns correspond to a concentration equal to 50 µM; the columns with horizontal hatching correspond to a concentration equal to 5 µM; the white columns correspond to a concentration equal to 0.5 µM; the grey columns correspond to a concentration equal to 100 nM and the cross-hatched columns correspond to a concentration equal to 50 nM.
Figure 4B:
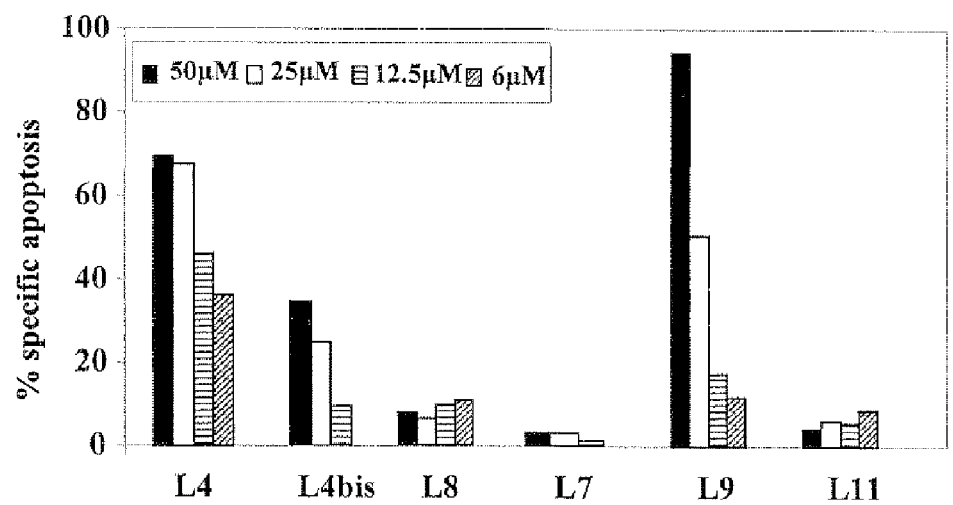

FIG. 4B represents the percentage of apoptosis specific to the BL41 Burkitt lymphoma cells (4.10⁵ cells/ml) after culture for 24 hours in the presence of different concentrations of the ligands L4, L4a, L8, L7, L9 and L11. The black columns correspond to a concentration equal to 50 µM; the white columns correspond to a concentration equal to 25 µM; the columns with horizontal hatching correspond to a concentration equal to 12.5 µM and the columns with oblique hatching correspond to a concentration equal to 6 µm.

Apoptosis is measured by flow cytometry after labelling with annexin V FITC and propidium iodide. Cells labelled with annexin V alone or with annexin V and propidium iodide are considered apoptotic. The percentage of specific apoptosis is calculated by the following formula:

[(% apoptosis with ligand–% apoptosis without ligand)/(100–% apoptosis without ligand)]×100

FIG. 5A represents the percentage of MRL-$^{lpr}$ mice (Koopman et al., 1998) alive at different ages after intravenous injection of 100 µL/mouse of PBS containing or not containing 100 µg of ligand L4. The injections took place at the ages of 7, 9 and 11 weeks. The solid line curve corresponds to an injection of PBS without ligand L4 and the dotted line curve corresponds to an injection of PBS with ligand L4.

FIG. 5B represents the percentage of MRL-$^{lpr}$ mice having anti-DNA antibodies (evaluated by an ELISA test) in their serum at different ages after the same treatment as in FIG. 5A. The white columns correspond to an injection of PBS without ligand L4 and the black columns correspond to an injection of PBS with ligand L4.

FIG. 5C represents the percentage of MRL-$^{lpr}$ mice having positive proteinuria in their urine at different ages after the same treatment as in FIG. 5A. The white columns correspond to an injection of PBS without ligand L4 and the black columns correspond to an injection of PBS with ligand L4. * All of the mice treated with ligand L4 died.

Figure 6:
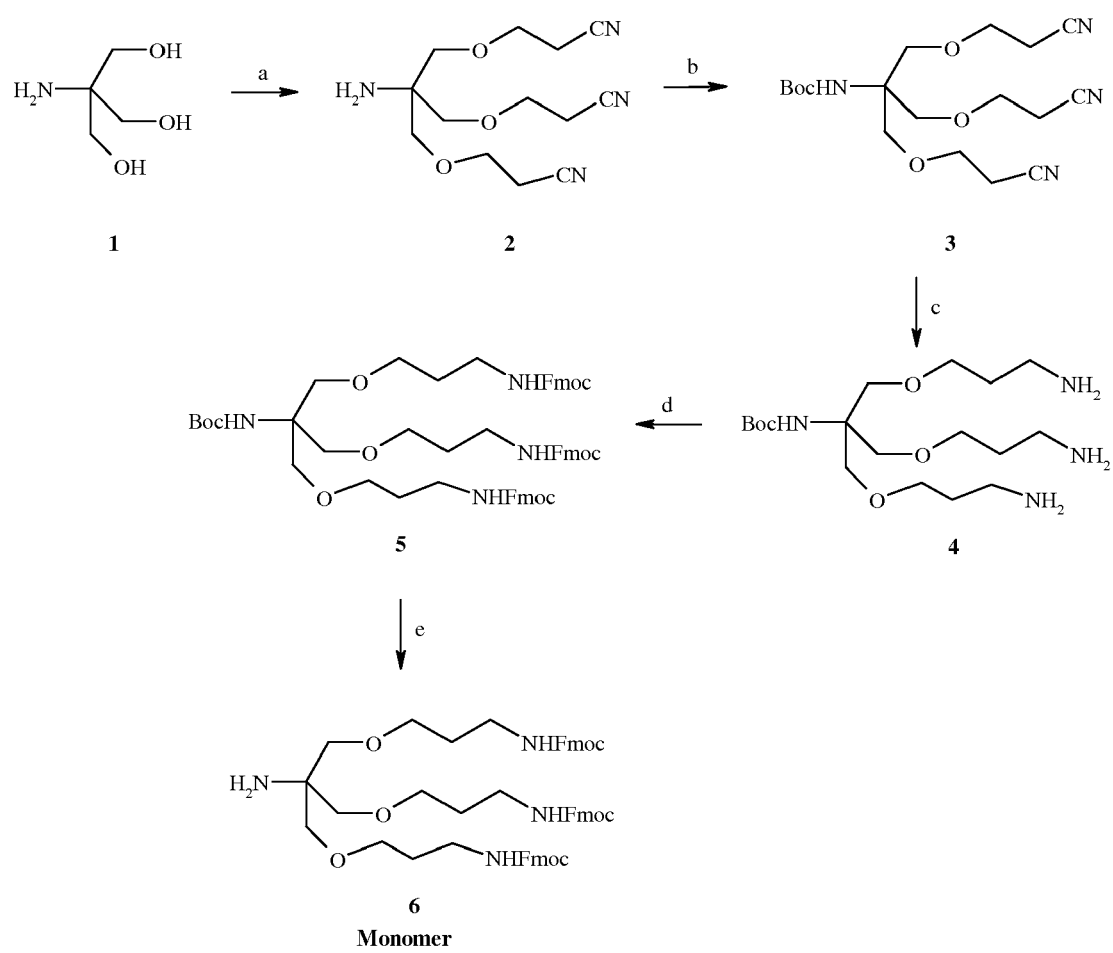

FIG. 6 is a reaction diagram of the preparation of monomer 6 (intermediate product) in the preparation of compound L7.

Figure 7:
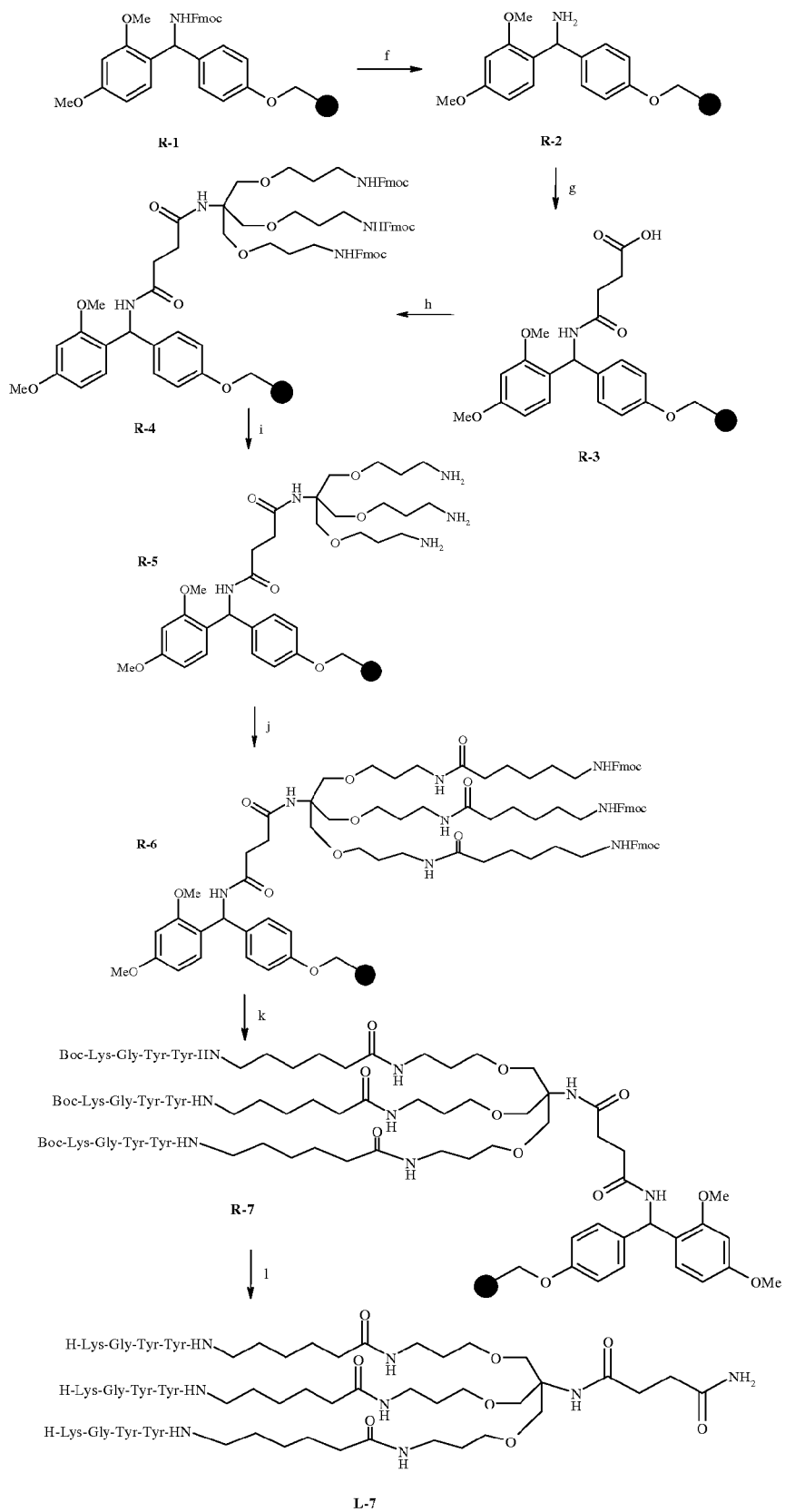

FIG. 7 is a reaction diagram of the preparation of compound L7.

Figure 8:
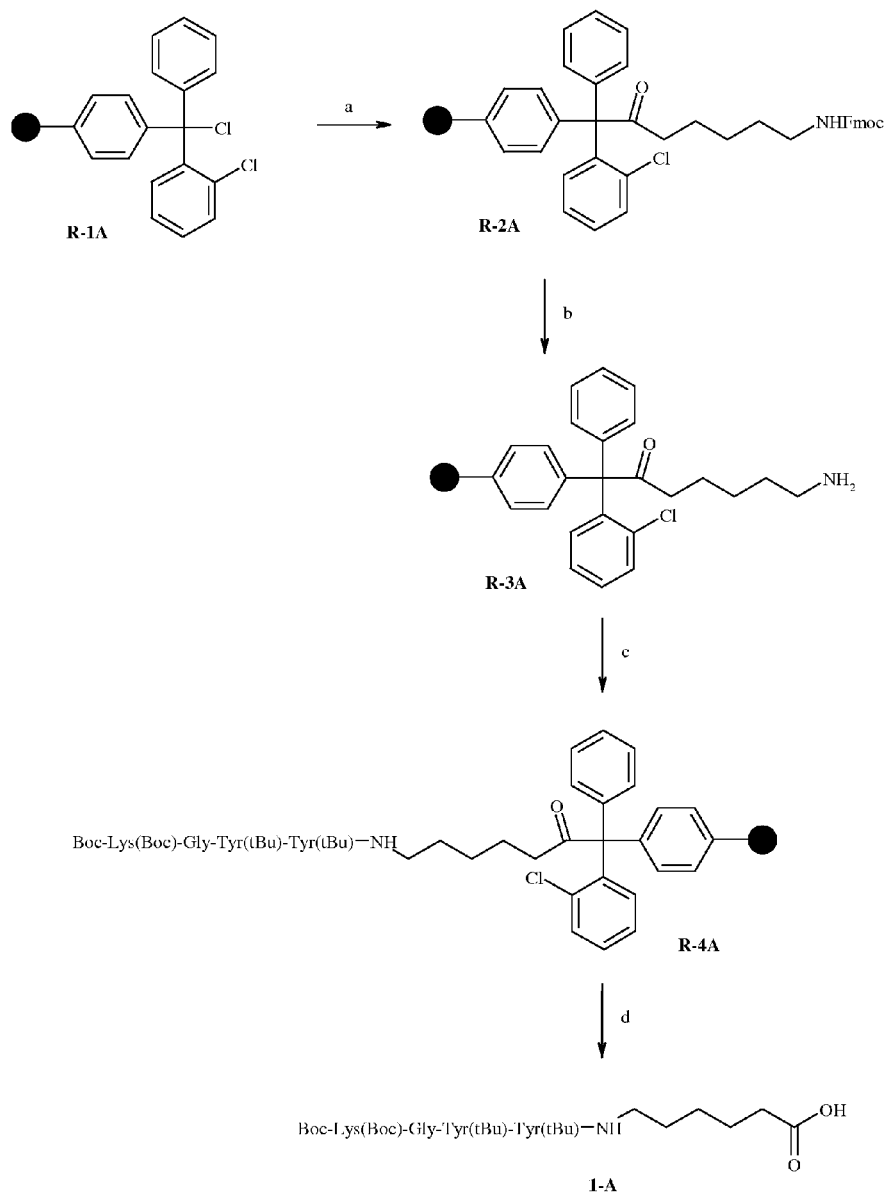

FIG. 8 is a reaction diagram of the preparation of compound L11.

Figure 9:
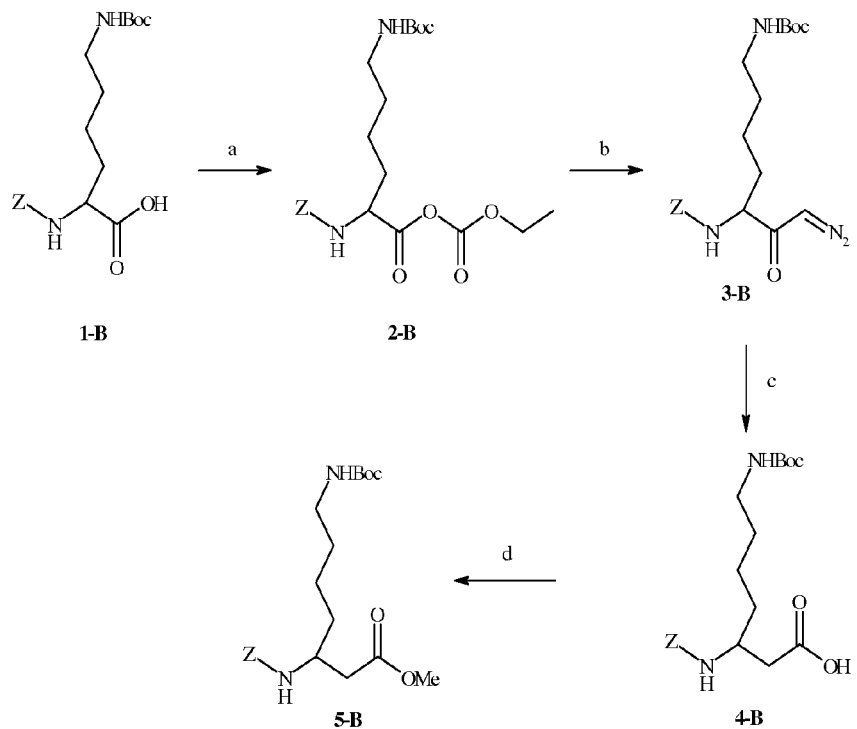

FIG. 9 is a reaction diagram of the preparation of Z-beta-Lys(Boc)-OH and Z-beta-Lys(Boc)-OMe in the preparation of compound L9.

Figure 10:
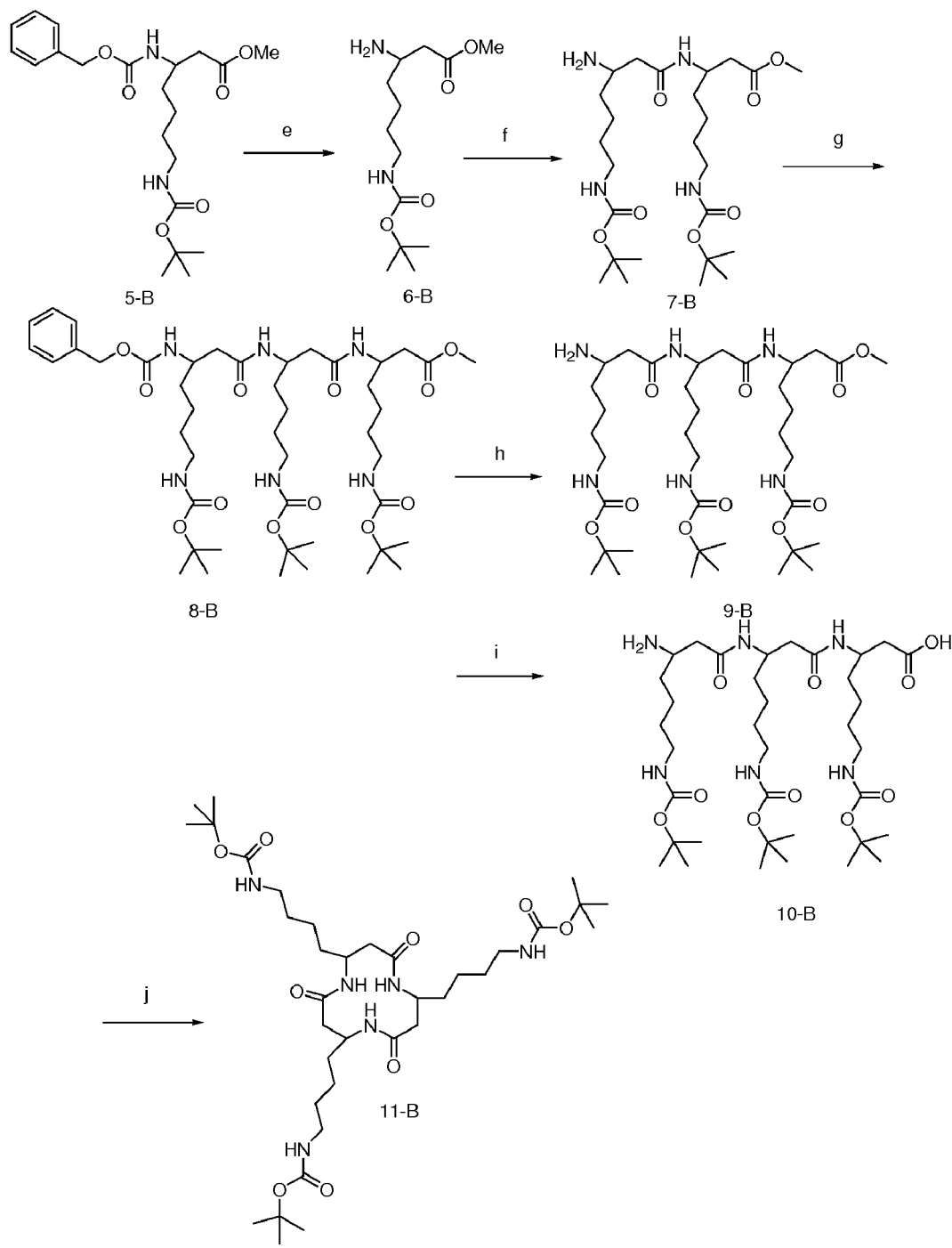

FIG. 10 is a reaction diagram of the construction of the protected core molecule in the preparation of compound L9.

Figure 11:
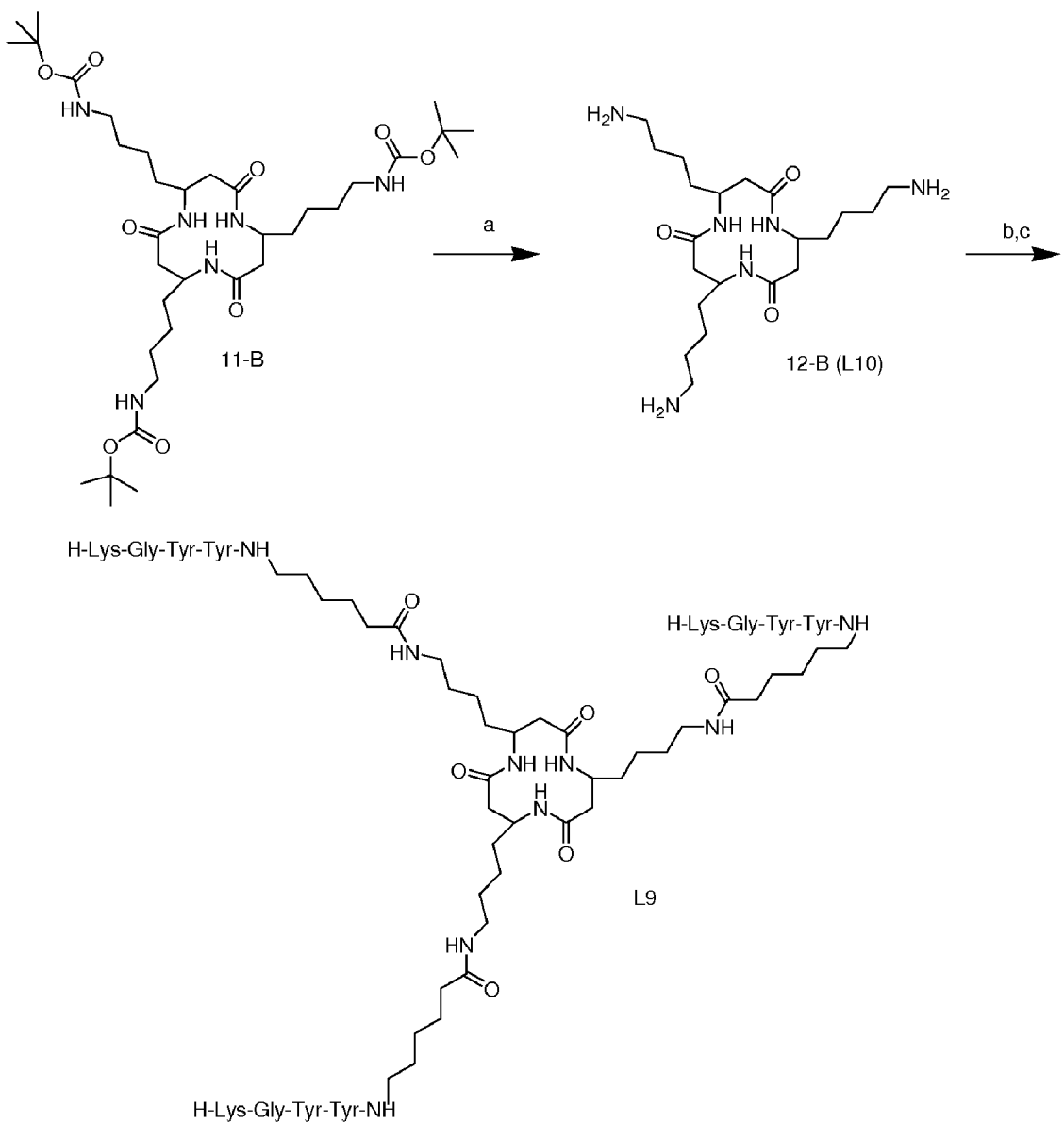

FIG. 11 is a reaction diagram of the deprotection of the core molecule and the synthesis of compound L9.

Figure 12:
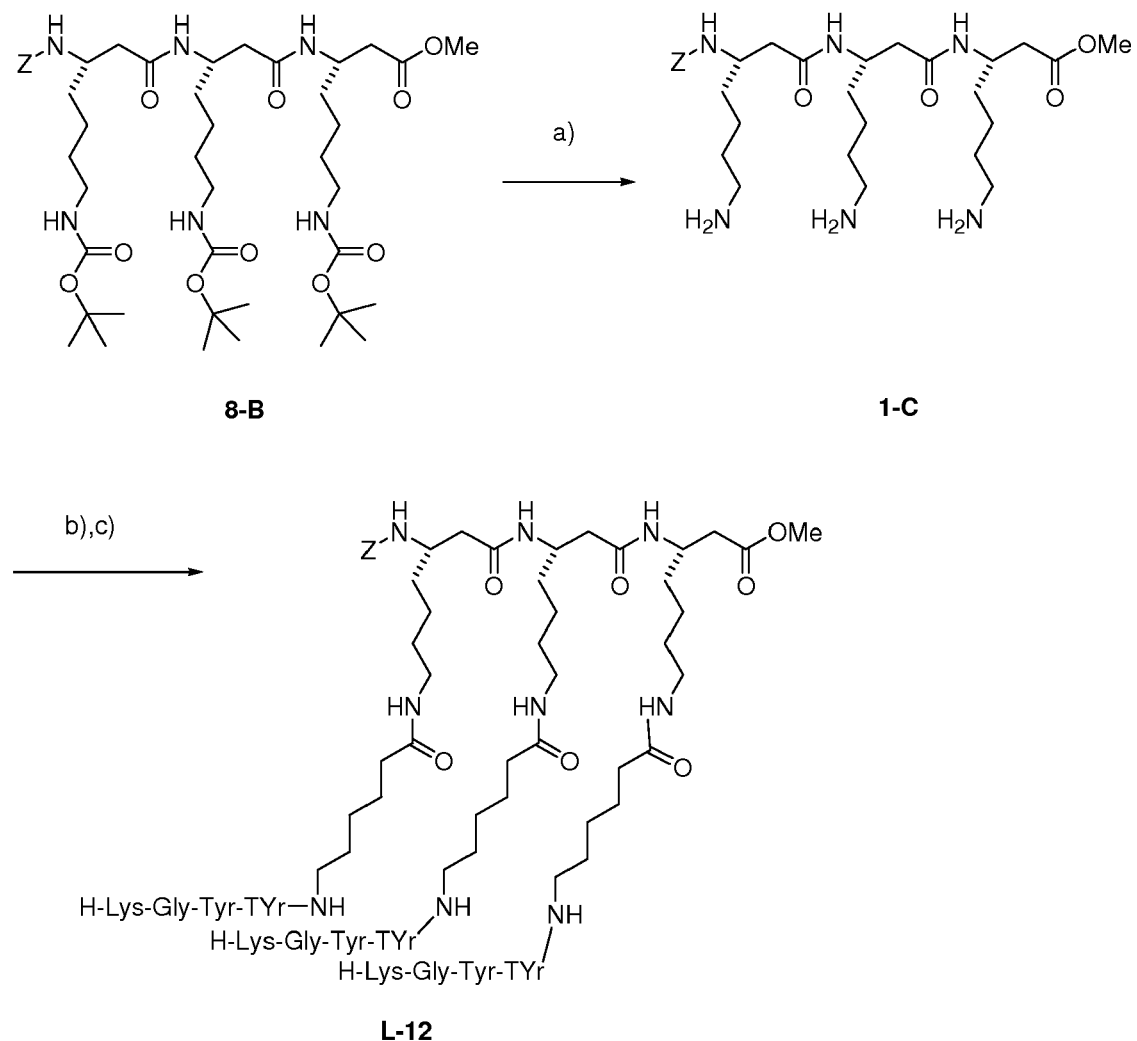

FIG. 12 is a reaction diagram of the preparation of compound L12.

PREPARATION OF COMPOUNDS L1, L2, L3 AND L4

A) Preparation of Compound L1

Compound L3 corresponds to the following formula (peptide sequence KGYY disclosed as SEQ ID NO: 3):

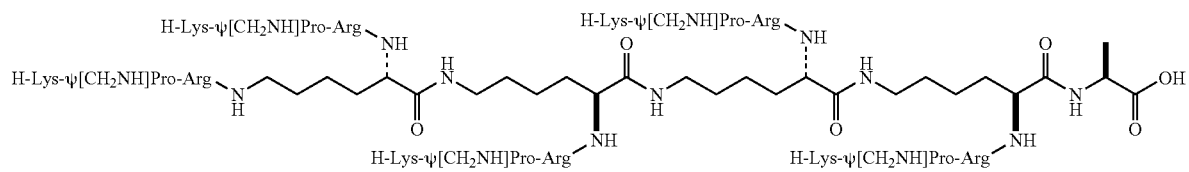

Compound L1 is synthesized in solid phase on a commercial Wang-Ala-Fmoc resin on a scale of 200 mmol. After cleavage of the Fmoc group with 25% piperidine in DMF (dimethylformamide) (2×15 minutes), the Fmoc-Lys(Mtt)-OH amino acid (3 equivalents) activated with Bop (benzotriazol-1-yloxy-tris(dimethylamino)phosphonium hexafluorophosphate) (3 equivalents), HOBt (1-hydroxybenzotriazole) (3 equivalents) and DIEA (diisopropylethylamine) (9 equivalents) in DMF is coupled to the resin (2×15 minutes). The techniques of resin washing and filtration as well as of deprotection of the Fmoc group are those commonly used in solid phase peptide synthesis. The Mtt (4-methyltrityl) group is cleaved with a solution (6 ml) of 85% DCM (dichloromethane), 10% TIS (triisopropylsilane), DMF (2×15 minutes), the free amine groups are acetylated with a solution of acetic anhydride (1 ml) in DCM (2 ml) in the presence of DIEA (1 ml) for 15 minutes. The product is cleaved from the resin with a solution (5 ml) of 80% TFA, 10% DCM, 10% TIS over 2 hours. After precipitation from cold ether, the crude product is lyophilized in an H$_2$O/acetonitrile/acetic acid mixture (80/15/5). The product is checked by mass spectrometry (MALDI-MS) and analytical HPLC and purified by preparative HPLC on a C$_{18}$ column using a gradient of acetonitrile in water.

C) Preparation of Compound L3

Compound L3 corresponds to the following formula:

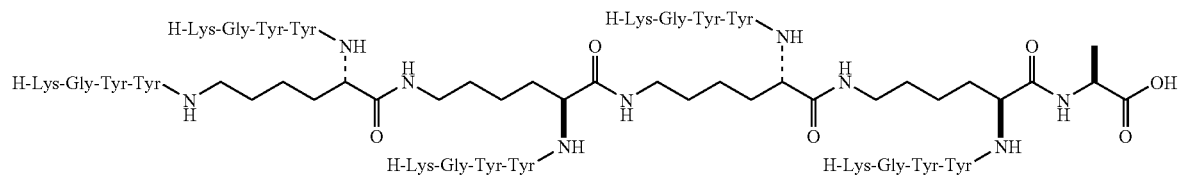

5% TFA (trifluoroacetic acid) (3×3 minutes). The second and third Fmoc-Lys(Mtt)-OH are coupled with the same strategy and the same quantities of reagents above. The fourth lysine is coupled in the form of Fmoc-Lys(Fmoc)-OH. After deprotection of the Fmoc group with 25% piperidine in DMF (2×15 minutes), the Fmoc-Arg(Pbf)-OH and Fmoc-Pro-OH amino acids (15 equivalents) activated with Bop (15 equivalents), HOBt (15 equivalents) and DIEA (45 equivalents) in DMF are coupled over 15 minutes (each coupling is repeated twice). The reduced amide bond between the lysine and the proline is formed on the resin using the reductive amination reaction of Boc-Lys(Boc)-CHO aldehyde (2.5 equivalents) in the presence of NaBH$_3$CN (2.5 equivalents) in DMF containing 1% acetic acid (2×1 hour). The product is cleaved from the resin with a solution (5 ml) of 80% TFA, 10% DCM, 10% TIS over 2 hours. After precipitation from cold ether, the crude product is lyophilized in an H$_2$O/acetonitrile/acetic acid mixture (80/15/5). The product is checked by mass spectrometry (MALDI-MS (Matrix assisted laser desorption ionization mass spectrometry)) and analytical HPLC and purified by preparative HPLC on a C$_{18}$ column using a gradient of acetonitrile in water.

B) Preparation of Compound L2

Compound L2 corresponds to the following formula:
Compound L2 is synthesized as L1 up to the fourth lysine. After deprotection of the Fmoc group with 25% piperidine in Compound L3 is synthesized as L1 up to the fourth lysine. After deprotection of the Fmoc group with 25% piperidine in DMF (2×15 minutes), the Fmoc-Tyr(tBu)-OH, Fmoc-Tyr(tBu)-OH, Fmoc-Gly-OH and Fmoc-Lys(Boc)-OH amino acids (15 equivalents) activated with Bop (15 equivalents), HOBt (15 equivalents) and DIEA (45 equivalents) in DMF are coupled over 15 minutes (each coupling is repeated twice). The product is cleaved from the resin with a solution (5 ml) of 80% TFA, 10% DCM, 10% TIS over 2 hours. After precipitation from cold ether, the crude product is lyophilized in an H$_2$O/acetonitrile/acetic acid mixture (80/15/5). The product is checked by mass spectrometry (MALDI-MS) and analytical HPLC and purified by preparative HPLC on a C$_{18}$ column using a gradient of acetonitrile in water.

D) Preparation of Compounds L4 and L4a

Compound L4 corresponds to the following formula (peptide sequence KGYY disclosed as SEQ ID NO: 3):

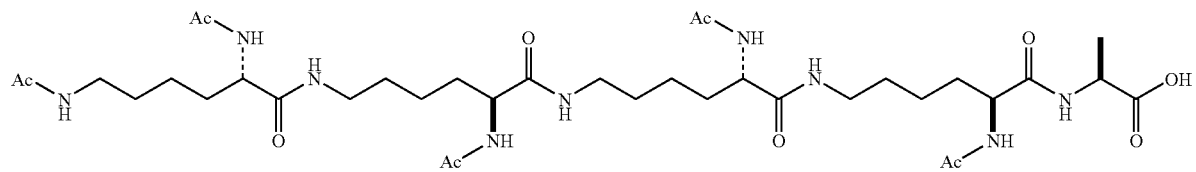

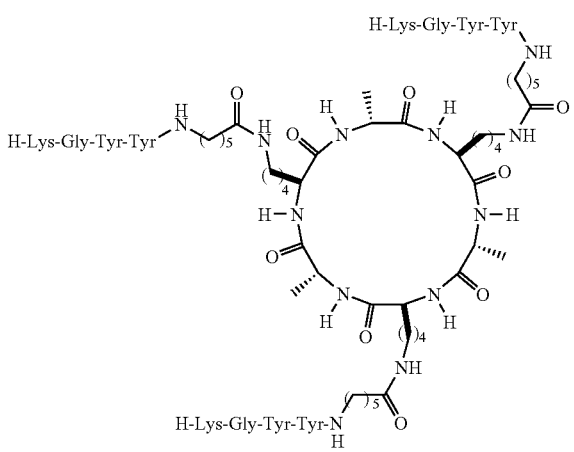

Compound L4a corresponds to the following formula (peptide sequence KGYY disclosed as SEQ. ID NO: 3):

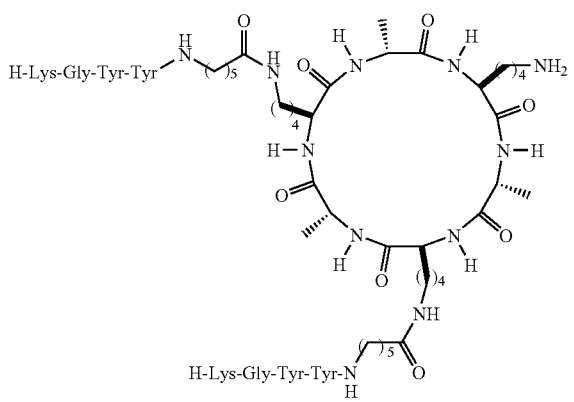

1) Preparation of Synthons a) Boc-(D)Ala-OAll

The Boc-D-Ala-OH amino acid (1.89 g, 10 mmol) is solubilized in 70 ml of ACN (acetonitrile) and the solution cooled down to 0° C. After adding 1.5 ml (1.2 equivalents) of DBU (1,8-diazabicyclo[5,4,0]undecen-7-ene), a solution of allyl bromide (0.72 ml, 1 equivalent), in 10 ml of acetonitrile, is added dropwise for approximately 15 minutes. The reaction, followed by thin layer chromatography (TLC) takes place at ambient temperature over 21 hours. After evaporation of the acetonitrile, the crude product is dissolved in ethyl acetate and the organic solution is washed with 5% NaHCO$_3$, H$_2$O, 1N KHSO$_4$ and H$_2$O. After drying over Na$_2$SO$_4$ and evaporation of the organic phase, the product is recovered in the form of oil with a yield of 73%. The product is characterized by NMR and FT-IR spectroscopy, and used for the following reaction without subsequent purification.

b) HCl×H-(D)Ala-OAll

The Boc-D-Ala-OAll amino acid (1.67 g; 7.3 mmol) is solubilized in a solution of 5 ml of HCl (4 M) in dioxane under an argon atmosphere for 30 minutes. The reaction is followed by TLC. After evaporation of the acid solution, the product is obtained as a solid under vacuum with a yield of 90%. The product is characterized by NMR and FT-IR spectroscopy, and used for the following reaction without subsequent purification.

c) Fmoc-Lys(Mtt)-OAll

The Fmoc-Lys(Mtt)-OH amino acid (625 mg, 1 mmol) is solubilized in 5 ml of dichloromethane (DCM) in the presence of HOBt (1 equivalent) and EDC×HCl (EDC: 1-ethyl-3-(3-dimethylaminopropyl)carbodiimide methiodide) (1.1 equivalents). After 5 minutes, allyl alcohol (1 equivalent) and DMAP (4-dimethylaminopyridine) (0.1 equivalents) are added. After 27 hours, 0.5 equivalents of HOBt, EDC×HCl, allyl alcohol and 0.1 equivalents of DMAP are added. In total, the reaction takes place over 44 hours. After evaporation of the dichloromethane, the crude product is dissolved in ethyl acetate and the organic solution is washed with 5% NaHCO$_3$, H$_2$O, 1N KHSO$_4$ and H$_2$O. After drying over Na$_2$SO$_4$ and evaporation of the organic phase, the product is recovered in the form of oil with a yield of 94%. The product is characterized by NMR and FT-IR spectroscopy, and used for the following reaction without subsequent purification.

d) H-Lys(Mtt)-OAll

Fmoc-Lys(Mtt)-OAll (240 mg, 0.36 mmol) is solubilized in 20% of DEA (diethyl amine) in DCM (10 ml). The reaction, monitored by TLC, takes place over 5 hours after adding another 3 ml of DEA. After evaporation of the solution, the crude product is solubilized in diethyl ether and extracted with a 1 N KHSO$_4$ solution. The acid solution is basified with solid NaHCO$_3$ and the product re-extracted with ethyl acetate. The organic phase is washed with H$_2$O, dried over N$_2$SO$_4$ and evaporated. The product is recovered in the form of oil with a quantitative yield, and used for the following reaction.

2) Reductive Amination on Solid Support

The reductive amination reaction is carried out in solid phase on a commercial 2-(3,5-dimethoxy-4-formylphenoxy) ethyl polystyrene resin, on a scale of 62 µmol. HCl×H-D-Ala-OAll (10 equivalents) and NaBH$_3$CN (10 equivalents) are solubilized in DMF and added to the resin. The reaction, monitored by FT-IR spectrophotometry, takes place over 24 hours under stirring.

3) Preparation of the Linear Dipeptide, Precursor of L4 and L4a

The Fmoc-Lys(Mtt)-OH amino acid (5 equivalents) is solubilized in 1 ml of dichloromethane in the presence of collidine (14 equivalents) and activated with triphosgene (1.65 equivalents) for 1 minute. The solution is then added to the resin (62 µmol) and the coupling reaction takes place over 30 minutes. The resin is washed extensively with DCM, DMF and dried with ether.

4) Preparation of the Linear Tripeptide, Precursor of L4 and L4a

The dipeptide-resin conjugate (62 mol) is treated with Pd(Ph$_3$)$_4$ (2 equivalents), solubilized in 2 ml of a solution of DCM:AcOH (acetic acid):NMM (N-methyl morpholine) in a ratio of 1850:100:50 for 6 hours under argon. The reaction is monitored by FT-IR spectrophotometry. Then, HATU [O-(7-azabenzotriazol-1-yl)-1,1,3,3-tetramethyluronium hexafluorophosphate] (4 equivalents), HOAt (7-azabenzotriazol) (4 equivalents), CuCl$_2$ (0.5 equivalents) and collidine (9 equivalents) are added to the H-Lys(Mtt)-OAll amino acid (5.8 equivalents), solubilized in 1.5 ml of DMF and 600 µl of DCM. The solution is added to the resin (62 µmol) and the coupling reaction takes place over 2 hours. The resin is washed extensively with DMF, DCM, methanol, dried with ether and checked by FT-IR spectrophotometry.

5) Preparation of the Cyclic Hexapeptide L4 and L4a

After deprotection of the Fmoc group with 25% piperidine in DMF (2×15 minutes), the Fmoc-D-Ala-OH, Fmoc-Lys (Mtt)-OH and Fmoc-D-Ala-OH amino acids (5 equivalents) activated with Bop (5 equivalents), HOBt (5 equivalents) and DIEA (15 equivalents) in DMF are coupled over 1 hour (each coupling is repeated twice). The allyl group is cleaved with Pd(Ph$_3$)$_4$ (2 equivalents), solubilized in 2 ml of a solution of DCM:AcOH:NMM in a ratio of 1850:100:50 for 6 hours under argon. The Fmoc group is cleaved with a 25% solution of piperidine in DMF (2×15 minutes). The linear hexapeptide-resin derivative with free N- and C-terminal ends is cyclized in the presence of HOAt (4 equivalents), DIC (diisopropylcarbodiimide) (4.4 equivalents) in a solution of DMF/DCM 5:2 (2.1 ml) over 3 hours. The Mtt group is cleaved with a solution (2 ml) of 85% DCM, 10% TIS, 5% TFA (3×2 minutes). The Fmoc-Ahx-OH (H-Ahx-OH: 6-amino hexanoic acid), Fmoc-Tyr(tBu)-OH, Fmoc-Tyr(tBu)-OH, Fmoc-Gly-OH and Fmoc-Lys(Boc)-OH amino acids (15 equivalents) activated with Bop (15 equivalents), HOBt (15 equivalents) and DIEA (45 equivalents) in DMF are coupled over 1 hour (each coupling is repeated twice). The cyclic peptide is cleaved from the resin with a solution (3 ml) of 90% TFA, 5% H$_2$O, 5% TIS over 2 hours. The cleavage is repeated a second time under the same conditions over 3 hours. After precipitation from cold ether, both the product L4 and the by-product L4a are obtained, which are then lyophilized in an H$_2$O/acetonitrile/acetic acid mixture (80/15/5). The products are checked by mass spectrometry (MALDI-MS) and analytical HPLC, purified and separated by preparative HPLC on a C$_{18}$ column using a gradient of acetonitrile in water.

E) Preparation of Compound L7

The ligand L7 corresponds to the following formula:

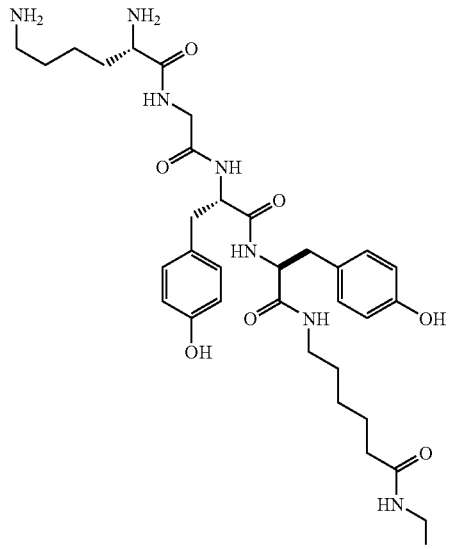

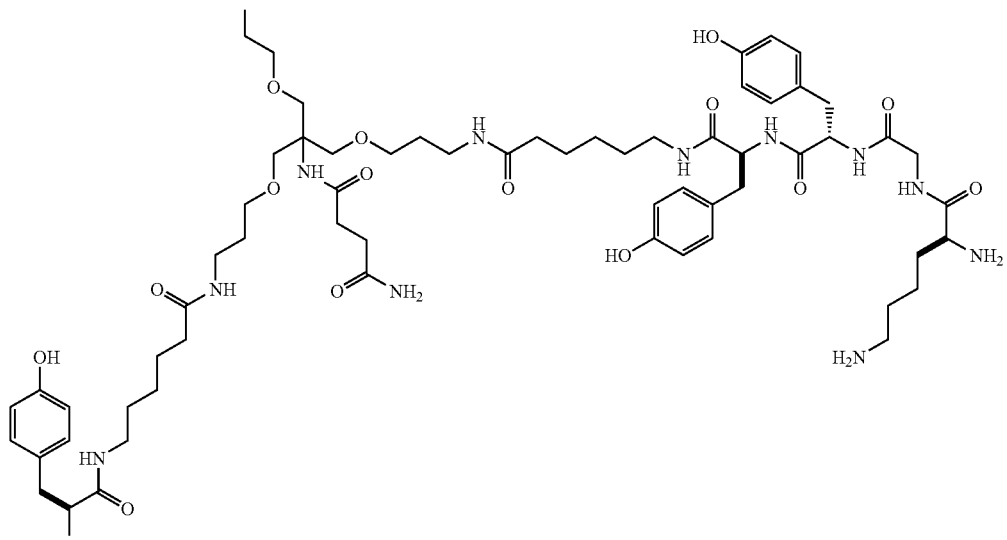

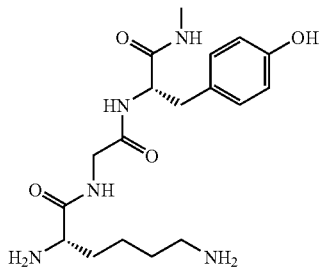

Reaction Diagram: Preparation of Monomer 6 (Intermediate Product)—FIG. 6 a. 2 g (1 eq.) of tris(hydroxymethyl)aminomethane 1 were dissolved in THF under stirring and 40% aqueous KOH was added, and then 4.34 ml (4 eq.) of acrylonitrile were added. The reaction mixture was maintained at ambient temperature under stirring for 24 hours. After evaporation of part of the THF, water was added and then extraction was carried out with dichloromethane (DCM), followed by drying over sodium sulphate. After the solvent was removed by evaporation, the crude product 2 was obtained. It was then purified by chromatography (EA/HEX/MeOH=3.5/3.5/1). Mass: 2.5 g; Yield: 54%.

b. 2 g (1 eq.) of compound 2 were dissolved in THF under stirring, and cooled down with an ice bath. 2.14 g (1.5 eq.) of $(Boc)_2O$ were dissolved in THF in another flask, which was then added slowly to the reaction medium, after having added 2.3 ml (1.5 eq.) of DIEA to the reaction medium. The reaction medium was kept overnight at ambient temperature and under stirring. After evaporation of part of the THF, ethyl acetate was added followed by sequential washing with $KHSO_4$(1N) $H_2O$, $NaHCO_3$ (st.) and NaCl (st.). Product 3 was then purified by chromatography (DCM/EA=10/1). Weight: 2.39 g; Yield: 71%.

c. Compound 3 was dissolved in $MeOH/CHCl_3$ (55/1). 10% $PtO_2$ was added and then the flask was flushed with hydrogen and maintained under a hydrogen atmosphere overnight. After filtration and evaporation of the solvent, compound 4 was obtained and dried under vacuum.

d. Compound 4 was dissolved in water under stirring. 6 eq. of $NaHCO_3$ were added in the form of powder. 3.6 eq. of FmocOSu were dissolved in THF and added to the reaction mixture. The reaction lasted 4 hours and then the THF was evaporated off. The remaining mixture was extracted with DCM, and then the organic phase was washed with a 1N $KHSO_4$ solution. After being dried over sodium sulphate, the solvent was removed by evaporation. The final compound was purified by chromatography (ethyl acetate/Hexane/acetic acid=3/7/0.5).

e. Compound 5 was dissolved in pure TFA under stirring for 30 minutes, and then the TFA was removed by evaporation in order to produce compound 6 (monomer). The overall yield of the last two stages is 73.3%.

The reactions on resins shown in FIG. 7 were carried out in a syringe under stirring.

f. Rink amide resin R-1 with a load of 0.62 mmol/g was swollen in dimethylformamide (DMF). The Fmoc group was removed by 25% piperidine/DMF. The reaction was carried out twice, each time for 20 minutes.

g. Resin R-2 was swollen in DCM and 10 eq. of succinic acid and 1 eq. of pyridine were added. The reaction was continued until the ninhydrin test was negative. The resin was filtered and washed with DCM and DMF.

h. Resin R-3 was swollen in DMF and then 6 eq. of compound 6 (monomer 1), 5 eq. of BOP (benzotriazol-1-yloxy-tris(dimethylamino)phosphonium hexafluorophosphate), 5 eq. of HoBt (1-hydroxybenzotriazole) and 15 eq. of DIEA (diisopropylethylamine) were added sequentially. Six hours later, the resin was filtered and washed with DMF, DCM, ether and dried under vacuum in order to produce R-4. The load is 0.24 mmol/g after quantitative UV assay of the fluorenyl group, and the overall conversion is 84%.

i. The Fmoc group was removed by 25% piperidine/DMF in order to produce R-5. The reaction was carried out twice, each time for 20 minutes.

j. Resin R-5 was swollen in DMF. 15 eq. of Fmoc-6-aminocaproic acid, 15 eq. of BOP, 15 eq. of HoBt and 60 eq. of DIEA were added and coupled over 4 hours in order to produce R-6. The reaction was verified by the ninhydrin test.

k. The Fmoc group was removed by 25% piperidine/DMF. 15 eq. of Fmoc-Xaa-OH, 15 eq. of BOP and 15 eq. of HoBt were dissolved in DMF, and then the solution was added to the resin, after having added 60 eq. of DIEA. For each amino acid, the coupling reaction was carried out twice, each time for 30 minutes. Finally, resin R-7 was verified by the ninhydrin test.

l. The synthesized peptide was cleaved with $TFA/H_2O$ (95/5) for 30 minutes and then the resin was filtered. The solution was recovered and precipitated from cold ether. After removing the ether, the final peptide L7 was dried and purified by HPLC and analyzed by mass spectrometry.

L-7 analogues were synthesized by following the same synthesis diagram but changing the peptide sequence for the interaction with CD40:

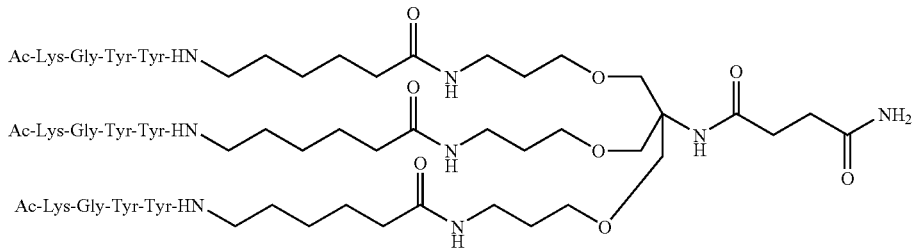

and the reverse sequence: H-Tyr-Tyr-Gly-Lys- (SEQ ID NO: 4) which will produce the construction L7-2 (peptide sequence YYGK disclosed as SEQ ID NO: 4)

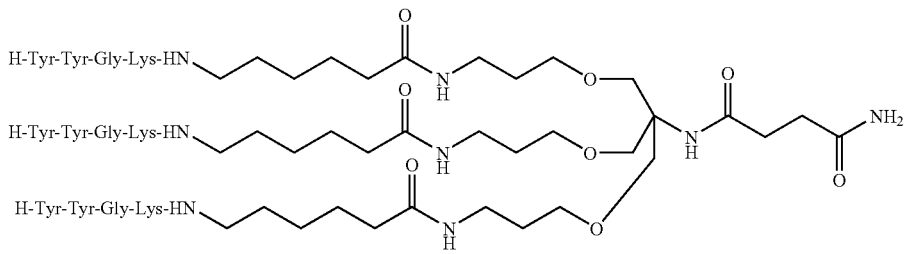

or modification of the spacer arm: replacement of the aminohexanoic acid by a glycine: L7-3 (peptide sequence KGYY disclosed as SEQ ID NO: 3)

L-7-3

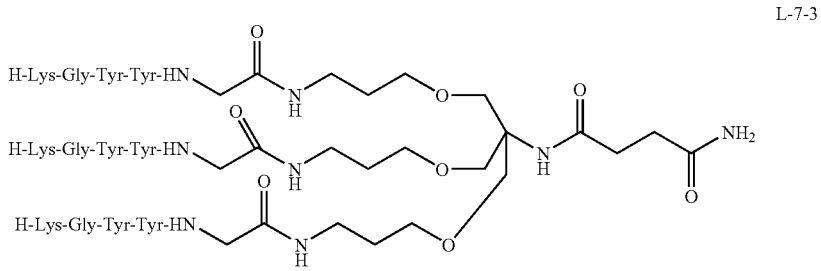

F) Preparation of Compound L11

The ligand L11 corresponds to the following formula (peptide sequences KGYY and K(Boc)-G-Y(tBu)-Y(tBu) disclosed as SEQ ID NOS 3 and 27, respectively):

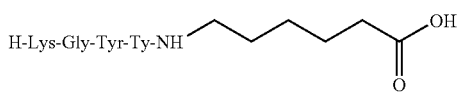

Reaction Diagram: FIG. 8

1) Preparation of the protected pentapeptide: Boc-Lys(Boc)-Gly-Tyr(tBu)-Tyr(tBu)-Ahx-OH The reactions on resins were carried out in a syringe under stirring (peptide sequence KGYY disclosed as SEQ ID NO: 3).

1.5 g (1 eq.) of 2-chlorotritylchloride resin (R1-A) (0.96 mmol/g) were washed twice with distilled DCM in a syringe under stirring. A mixture of 1.02 g (2 eq.) of Fmoc-6-aminocaproic acid and 1.5 ml (6 eq.) of DIEA in DCM was prepared and added to the resin. Three hours later, the resin was filtered and washed with DCM. It was again swollen in methanol under stirring for 1 hour. It was then filtered and washed with DMF, IpOH (isopropanol), DCM, ether. It was then dried under vacuum in order to produce R-2A.

Resin R-2A was treated with a solution of 25% piperidine/DMF for 20 minutes and the resin was then filtered in order to produce R-3A and the solution was recovered. The reaction was carried out twice. The load of resin 2 was 0.6 mmol/g by quantitative UV assay of the solution recovered and the conversion of the coupling reaction was 81%.

General process for the coupling of the amino acids: 5 eq. of Fmoc-Xaa-OH, 5 eq. of BOP and 5 eq. of HoBt were dissolved in DMF and then the mixture was added to the resin which was pre-swollen in DMF. 15 eq. of DIEA were added to the reaction system. The coupling reaction was carried out twice, each time for 30 minutes. The resin was tested by the ninhydrin test.

After repetition of these deprotection and coupling processes using the amino acids necessary for the synthesis of the peptide, resin R-4A was obtained.

Resin R-4A was placed in a syringe. A mixture of 1,1,1,3,3,3-hexafluoro-2-propanol and DCM (60/40) was added to the resin. The syringe was maintained under stirring for 2 hours and then the resin was filtered and the solution recovered. After evaporation of the solvent, the remaining product was precipitated from cold ether and then purified by HPLC in order to produce 1-A.

2) Peptide 1-A was treated with TFA in the presence of water and triisopropylsilane (95:5:5) in order to produce L11 which was precipitated from cold ether, centrifuged, lyophilized and purified by reverse phase HPLC(RP-HPLC).

G) Preparation of Compound L9

1) Preparation of Z-beta-Lys(Boc)-OH (4B) and Z-beta-Lys (Boc)-OMe (5B): FIG. 9 a) 40 mmol (1 eq.) of Z-Lys(Boc)OH was dissolved in 100 ml of THF under stirring. 5.27 ml (1.2 eq.) of NMM was added, the reaction mixture was then cooled down to −20° C. 4.59 ml (1.2 eq.) of ethyl chloroformate was dissolved in 30 ml of THF, and the mixture was then added dropwise to the reaction system. The reaction mixture containing 2-B was kept cold for another 20 minutes.

b) Preparation of Diazomethane:

7.76 g of KOH was dissolved in a mixture of 12.5 ml of water, 10 ml of ether and 35 ml of 2-(2-ethoxyethoxy)ethanol under stirring, followed by heating at 75° C. 15.52 g of diazald (N-methyl-N-nitroso-p-toluenesulphonamide; Aldrich) were dissolved in 140 ml of ether and the mixture was added dropwise to the reaction mixture. The diazomethane thus produced was condensed at −75° C. in an ice bath in acetone. The ethereal solution of diazomethane thus produced was added to the reaction solution of 2-B and then the reaction mixture was maintained at ambient temperature overnight. 1 ml of ethylamine (EA) was added and then a large quantity of $NaHCO_3$ (st.). After separation of the organic and aqueous phases, the organic phase was washed twice with $NaHCO_3$ and once with NaCl (st). After drying over sodium sulphate, the solvent was evaporated of and the diazoketone 3-B thus produced was dried under vacuum. Mass: 15.4 g; Yield: 95%.

c) Rearrangement Reaction:

7 g (1 eq.) of the diazoketone 3-B were dissolved in a mixture of 110 ml of THF and 18 ml of water under stirring in the absence of light and the mixture was cooled down to −20° C. 435 mg (0.11 eq.) of silver benzoate and 6.07 ml (2.5 eq.) of triethylamine were added. The reaction mixture was maintained at ambient temperature overnight in darkness. Part of the THF was evaporated off, 20 ml of ether was added which was extracted with $NaHCO_3$ several times. The aqueous phase was combined and acidified to pH 3 with $KHSO_4$ powder. The solution was extracted with DCM and dried over sodium sulphate. After evaporation of the solvent, the final product 4-B was dried under vacuum. Mass: 5 g; Yield: 73%.

d) 1.67 g (1 eq.) of 13 amino acid 4-B as obtained previously was dissolved in acetonitrile and the mixture was cooled down to 0° C. with an ice bath. After an hour, 1.32 ml (5 eq.) of iodomethane was added. The reaction mixture was maintained at ambient temperature overnight. The acetonitrile was evaporated off and ethyl acetate was added, which was washed sequentially with $NaHCO_3$(st.), $KHSO_4$ (1N) and NaCl (st.). The organic phase was dried over sodium sulphate and the solvent was removed by evaporation in order to produce 5-B. Mass: 1.53 g; Yield: 88%.

2) Construction of the Protected Core Molecule:

Reaction Diagram: FIG. 10 e) 765 mg (1 eq.) of compound 5-B was dissolved in ethanol under stirring and 10% Pd/C (by weight) was added. The flask was flushed with hydrogen three times and maintained under a hydrogen atmosphere for 2 hours. After filtration, the solvent was removed by evaporation and the remaining product 6-B was dried under vacuum. Mass: 400 mg; Yield: 98%.

f) 657 mg (1 eq.) of compound 4-B was dissolved in 3 ml of DMF under stirring and then 40 mg (1.1 eq.) of compound 6-B, 738 mg (1 eq.) of BOP and 726 μl (2.5 eq.) of DIEA were added sequentially. Two hours later, the reaction mixture was precipitated from $NaHCO_3$(st). After filtration, the solid was washed with $H_2O$, $KHSO_4$, NaCl(st.) and then dried under vacuum. Mass: 1 g; Yield: 84%. This compound was hydrogenated in MeOH in order to produce 7-B in a quantitative yield.

g) 1 equivalent of compound 4-B was dissolved in 3 ml of DMF under stirring and then 1.1 eq. of compound 7-B, 1 eq. of BOP, 2.5 eq. of DIEA were added sequentially. After two hours, the reaction mixture was precipitated from $NaHCO_3$ (st). After filtration, the solid was washed with $H_2O$, $KHSO_4$, NaCl(st.) and then dried under vacuum in order to produce 8-B.

h) 100 mg of compound 8-B was dissolved in methanol under stirring and 10% Pd/C (by weight) was added. The flask was flushed with hydrogen three times and maintained under a hydrogen atmosphere for 2 hours. After filtration, the solvent was removed by evaporation and the remaining product was dried under vacuum in order to produce 9-B. Mass: 78 mg; Yield: 92%.

i) 78 mg (1 eq.) of compound 9-B was dissolved in methanol and then 10 eq. of aqueous 2N NaOH were added. The reaction was monitored by thin layer chromatography TLC (solvents: ethyl acetate/pyridine/acetic acid/water). At the end of the reaction, the methanol was evaporated off and water was added. The mixture was acidified with acetic acid to pH 3 and a precipitate was formed. The solid was recovered by filtration and dried under vacuum in order to produce 10-B. Mass: 50 mg; Yield: 65%.

j) 50 mg (1 eq.) of compound 10-B was dissolved in 3 ml of DMF and 42 μl (3.5 eq.) of DIEA were added. 36 mg (1.2 eq.) of BOP were dissolved in 3 ml of DMF under stirring. The solution prepared previously was added dropwise. The reaction mixture was maintained at ambient temperature for 2 days and then precipitated from $NaHCO_3$(st.). The precipitate was recovered and washed with $H_2O/KHSO_4$ and $H_2O$, then dried under vacuum in order to produce 11-B. Mass: 37 mg; Yield: 76%.

3) Deprotection of the Core Molecule and Synthesis of L-9

Reaction Diagram (Peptide Sequence KGYY Disclosed as SEQ ID NO: 3): FIG. 11 a) 50 mg (1 eq.) of compound 11-B were dissolved in TFA under stirring for 30 minutes and then the TFA was removed by evaporation. The product was dried under vacuum in order to produce 12-B (also named L10).

b) Compound 12-B was dissolved in DMF under stirring. 217 mg (3.3 eq.) of the pentapeptide 1-A which is synthesized in solid phase as described above, 100 mg (3.3 eq.) of BOP, 39.5 μl (10 eq.) of DIEA were added to the reaction system. The reaction lasted 25 hours and then the reaction mixture was precipitated from a large quantity of $NaHCO_3$(aq.). The precipitate was filtered and washed with $H_2O/KHSO_4$, $H_2O$ and ethylamine (EA). The solid was dried under vacuum in order to produce 13-B. Mass: 153 mg; Yield: 69%.

c) Treatment of 13-B with TFA produced the compound of the title in a quantitative yield. Pure compound L9 was obtained by purification by RP-HPLC (reversed-phase chromatography).

H) Preparation of L12 (Peptide Sequence KGYY Disclosed as SEQ ID NO: 3): FIG. 12 a) 1 equivalent of compound 8-B was dissolved in TFA under stirring for 30 minutes and then the TFA was removed by evaporation. The product was dried under vacuum in order to produce 1-C.

b) Compound 1C was dissolved in DMF under stirring. 3.3 eq. of the pentapeptide 1-A which is synthesized in solid phase as described above, 3.3 eq. of BOP and 10 eq. of DIEA were added to the reaction system. The reaction lasted 25 hours and then the reaction mixture was precipitated from a large quantity of $NaHCO_3$(aq.). The precipitate was filtered and washed with $H_2O/KHSO_4$, $H_2O$ and ethylamine. The solid was dried under vacuum in order to produce 2-C. Mass: 153 mg; Yield: 69%.

c) Treatment of 2-C with TFA produced compound L-12 in a quantitative yield. Pure compound L-12 was obtained by purification by RP-HPLC chromatography.

Biological Tests:

These tests are carried out in 3 phases. Firstly, the most interesting ligands are chosen by simple tests, then their physiological effects are tested in cellular activation models in vitro. Finally, the most interesting ligands are tested in murine models in vivo.

I—Selection of the Ligands:

Once the structural integrity of these ligands has been analysed, their binding is tested on soluble or membranous CD40 molecules. To do this, the inhibition of the binding of CD40L which is soluble on the CD40 molecule adsorbed to plastic or presented by normal or transformed B cells (Burkitt's lymphoma). This stage is evaluated using an ELISA test and flow cytometry labelling allowing visualisation of the CD40/CD40L binding.

Then, the affinity of these ligands for the CD40 molecule is evaluated using a biosensor (BIAcore™). The agonist or antagonist effect of the ligands was tested using two simple biological tests. In the first, the expression of the membranous molecule CD95 by transformed B cells (Burkitt's lymphoma) is studied after activation by the CD40-CD40L interaction (Schattner et al., 1996). In such a model, the CD40L partner is expressed on transfected fibroblasts (3T6-CD40L) (Buelens et al., 1997). The BL41 Burkitt's lymphoma cells are incubated with non-transfected 3T6 fibroblasts (FIGS. 3A and 3C) or with 3T6 fibroblasts transfected by CD40L (FIGS. 3B and 3D). After 48 hours, the expression of CD95 is evaluated by flow cytometry. The expression of CD95 is induced in the presence of CD40L (FIG. 3B). A commercial anti-CD40L antibody inhibits the consequences of the CD40-CD40L interaction (FIG. 3D).

The second test is based on the property of certain B lymphomas to cease proliferation and enter apoptosis during the bridging of their membranous CD40 molecule (Tong et al., 1999). In this test, the BL41 cells are incubated with ligands CD40 and after 24 hours either the inhibition of proliferation of these cells is measured, by studying the incorporation of tritiated thymidine, or the percentage of apoptotic cells is measured with a flow cytometry study (FIGS. 4A and 4B).

The agonist effect of the ligands is evaluated by measurement, after incubation of the B cells, with ligands or of the expression of CD95 with flow cytometry or of the inhibition of the proliferation and/or of the increase in death by apoptosis.

The antagonist effect is evaluated by measurement of the decrease in the expression of CD95 induced by the CD40L in the presence of the different chemical ligands (see Table I).

With the help of these tests, the most interesting ligands are chosen to evaluate their activity in vivo and in vitro in more complex models.

A) Principle of the Biological Tests

1—Expression of CD95 Induced by CD40L

The lymphoma B cells express the CD95 molecule when they receive a signal via the CD40 molecule, which they express in a constitutive manner. This signal is generally conveyed by the CD40L (CD154) molecule expressed by another cell. The antagonist ligands inhibit the binding of CD40 on CD40L and thus mimic the expression of CD95. The agonist ligands copy the CD40L molecule and induce the expression of CD95 even in the absence of the cell expressing CD40L.

Operating Method

The BL41 Burkitt's lymphoma cells ($5.10^5$/ml) are cultured in the presence of 3T6 fibroblasts ($10^5$/ml) transfected (3T6-CD40L) or not transfected with CD40L (3T6), and treated with mitomycin to stop their proliferation. The ligands are added at the start of the culture at the chosen concentration. After culture for 48 hours, expression of the CD95 molecule is measured by flow cytometry. The BL41 cells are distinguished from the fibroblasts using an anti-CD19 antibody (specific marker of the B cells).

Results

Figure 2:
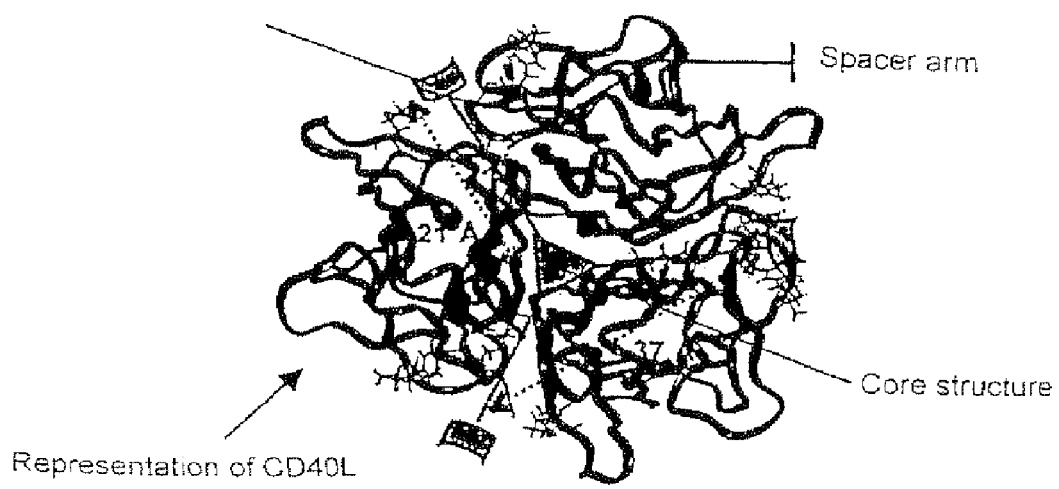
FIG. 2 represents the structure of the trimeric ligands of the invention.
Figure 3A:
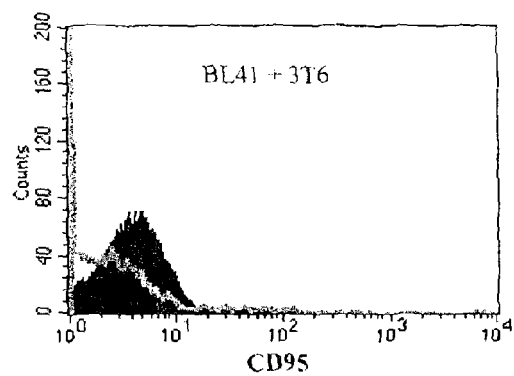
FIGS. 3A, 3B, 3C and 3D represent the expression of CD95 at the surface of the BL41 Burkitt lymphoma cells during the CD40-CD40L interaction, measured by flow cytometry. The grey surfaces represent the isotypical control and the light grey curve represents the fluorescence proportional to the quantity of anti-CD95 fixed on the cells.
Figure 3B:
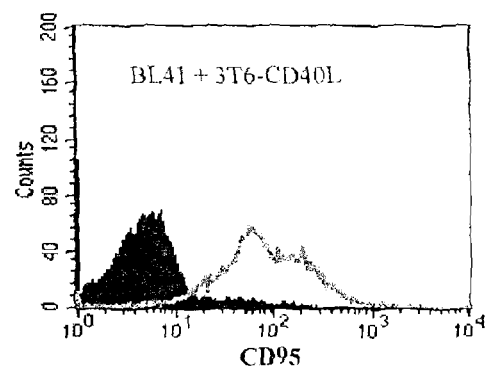
Figure 3C:
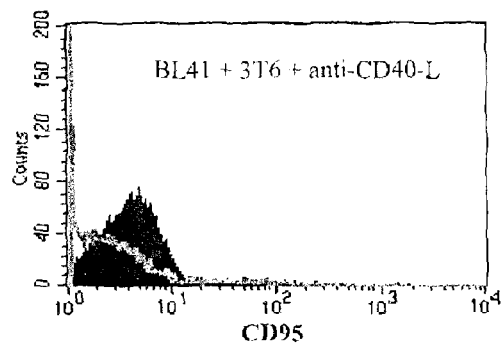
Figure 3D:
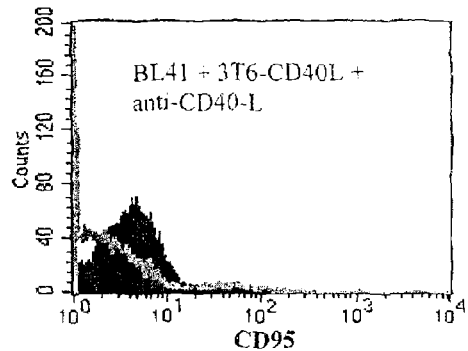

The BL41 cells cultured in the presence of 3T6 cells do not express the CD95 molecule (FIG. 3A). On the other hand, the expression of CD95 is induced at the surface of the BL41 cells in the presence of 3T6-CD40L cells (FIG. 3B). A commercial anti-CD40L antibody, which blocks the CD40/CD40L interaction, completely inhibits the expression of CD95 induced on the BL41 cells in the presence of 3T6-CD40L cells (FIG. 3D).

The expression of CD95 is inhibited by the ligand L1 at 100 and 50 μM (Table 1). The ligand L3, which has the same core structure as L1, but which has a different amino acids sequence greatly inhibits the expression of CD95 induced by CD40L from 100 to 25 μM. The ligand L2, which corresponds to the core structure of the ligands L1 and L3, has no effect on the expression of CD95. The ligand L7, constituted by a branched core structure having the same peptide sequence as L3, has no effect on the expression of CD95 induced by CD40L. On the other hand, the ligand L4, with a cyclic core structure having 3 examples of the peptide sequence mimicking the CD40-CD40L interface, inhibits the expression of CD95 induced by CD40L for a range of concentrations from 50 to 0.5 μM. Its activity is therefore approximately 10 times greater than the linear ligand which has the same peptide (L3). It is interesting to note that the maximum inhibition is obtained for a concentration of 10 μM, the concentration of 50 μM inducing a substantial cell mortality (cf. part 2). The ligand L4a which is constituted by the same core molecule but which has only 2 examples of the peptide sequence mimicking the CD40-CD40L interface only very weakly inhibits the expression of CD95 induced by CD40L.

TABLEAU I

| | % of inhibition of the expression of CD95 induced by CD40L after treatment with | | | | | |
|---|---|---|---|---|---|---|
| | L1 | L2 | L3 | L4 | L4a | L7 |
| 100 μM | 60 | 0 | 60 | | | |
| 50 μM | 43 | 0 | 62 | 22 | 13 | 0 |
| 25 μM | 0 | 0 | 25 | | | |
| 10 μM | | | 13 | 40 | | |
| 5 μM | | | 0 | 36 | 8 | 0 |
| 0.5 μM | | | | 19 | 0 | 0 |

2—Induction of the Apoptosis of B Lymphomas by CD40L

Certain B lymphomas enter apoptosis when their CD40 molecule is bridged by an anti-CD40 antibody or by CD40L which is soluble independently from the CD95 molecule. This induction of apoptosis is expressed as a decrease in proliferation measured by the incorporation of tritiated thymidine. The agonist ligands of CD40 will induce an increase in apoptosis and as a result a decrease in the incorporation of tritiated thymidine.

Operating Method

The BL41 Burkitt's lymphoma cells ($4.10^5$/mL) are cultured in the presence of the different ligands at the chosen concentration. After 24 hours, the cells are either incubated for 8 hours with tritiated thymidine (1 µci/well) to measure the proliferation or are labelled with Annexin V-FITC and propidium iodide to evaluate the percentage of apoptotic cells with flow cytometry.

Results

The ligand L4 (cyclic structure core+3 examples of the peptide sequence mimicking the CD40-CD40L interface) like the soluble CD40L molecule greatly inhibits the proliferation of BL41 cells. However the ligand L7 (branched core structure having the same peptide sequence as L4) and its derivatives L7-1, L7-2 and L7-3 only have a small or no effect on the proliferation of the BL41 cells (FIG. 4A).

This inhibition of proliferation is accompanied for the ligand L4 by a strong increase in apoptosis while the ligand L4a (cyclic core structure+2 examples of the peptide sequence) induces a very weak apoptosis. The ligand L8 constituted by the single core structure or the ligand L11 constituted by the single peptide sequence have no effect on the death by apoptosis of the BL41 cells (FIG. 4B).

The ligand L9 which is constituted by a cyclic core structure which is different to that of the ligand L4 having 3 examples of the same peptide sequence induces the apoptosis of BL41 just as strongly (FIG. 4B).

In conclusion, the ligands L4 and L9 have an agonist activity and mimic CD40L.

B) Study of the Interaction Between CD40 and CD40L and the Ligands L1 to L12:

Principle of the Method

The Biacore3000 is a device which allows the interactions between two molecules to be studied, based on the surface plasmon resonance. It allows measurement in real time, and therefore allows the kinetics of interaction (association and disassociation) of an analyte (which is in an injected solution) and of a ligand (immobilised on a microchip supporting the measurement) to be monitored. The kinetic measurements at different concentrations of analyte allow calculation of the affinity constants of the interaction between the ligand and the analytes. The microchip contains four cells for different measurements, which allows direct comparison of a reference cell on which a protein which is not pertinent (protein which has no affinity with the ligand studied), but close to the ligand is immobilised with the cell on which the ligand is immobilised.

Operating Method

Rabbit antibodies directed against the constant region of mouse immunoglobulins were immobilized on a microchip. In the reference cell a monoclonal mouse antibody of isotype IgG2a (LG112) at 40 nM is immobilized with a flow of 5 µL/min for 2 minutes; in the cell of the ligand the recombinant CD40 associated with the constant region of the mouse IgG2a heavy chain (human CD40 muIg fusion protein, ANCELL Corporation, Bayport, Minn.) is immobilized under the same conditions.

On the two cells (reference and ligand), the CD40L (human CD154 muCD8 fusion protein, ANCELL Corporation) at different concentrations or the CD40L at a concentration of 1 µM or of 125 nM, are injected, as analyte, in the presence of different concentrations of ligands. The flow in the presence of the analytes is 10 µL/min for 5 minutes to study the association and, in the absence of analytes, the conditions are the same to study the dissociation.

In order to regenerate the cells (i.e. remove all the proteins adsorbed in a non-covalent manner), a solution of 10 mM of HCl is injected at 5 µL/min for 1 minute. The cells are then ready for another analysis.

Results

In order to study the affinity constant of the CD40L for the CD40, 4 concentrations of CD40L from 62.5 to 500 nM are used. The equilibrium constant is calculated at 54 nM.

To study the association with L1, the analyte was constituted by CD40L at 1 µM and L1 at 50 µM. Although an inhibition is observed during the first seconds of the interaction, it disappears during the five minutes of association, making the calculation of the equilibrium constant of L1 impossible. This is therefore greater than 50 µM.

The association of L3 was studied in the presence of 125 nM of CD40L. The kinetic analysis in the presence of 2.5 µM of L3 produced an equilibrium constant for L3 of 10 µM.

The association of L4, L7 (and of its derivatives), L8, L9 L11 and L12 was studied in the presence of 100 nM of CD40L. Only the L4 and L9 molecules bind to CD40 and displace CD40L. The kinetic analysis in the presence of 40 and 80 nM of L4 produced an equilibrium constant for L4 of 180 nM. The ligand L4 inhibited 50% of the binding of CD40L (IC50) at 80 nM. The ligand L9, tested under the same conditions, has an IC50 which is less than 50 nM, its equilibrium constant is therefore less than that of L4. It is interesting to note that the molecule which is a linear version of L9 does not bind to CD40. These results suggest that the conception of active CD40 ligands requires the use of a core molecule (A in the general formula: A-$X_n$) sufficiently rigid and with C3 symmetry.

II—Tests of the Ligands in Models In Vitro:

The immature dendritic cells, differentiated in vitro from human monocytes, are very sensitive to CD40L which induces their maturation. This maturation is accompanied by (i) profound phenotype rearrangements, (ii) a secretion of cytokines and chemokines, (iii) a resistance to the apoptosis mediated by CD95 (Koppi et al., 1997; Bjorck et al., 1997), (iv) an increased dendritic cell longevity (Miga et al., 1997) and (v) a clearly increased capacity of the mature dendritic cells to stimulate allogenic T lymphocytes. The effect of these ligands on the CDs is studied. Firstly, the capacity of potential agonist ligands to modify the phenotype of the immature CDs is studied with flow cytometry. This study is continued by seeking to demonstrate, using ELISA tests, the triggering of a secretion of cytokines by the agonist ligands. Finally, this research is completed by studying the capacity of the CDs, preincubated in the presence of the agonist molecules, to stimulate the allogeneic T cells. The effect of the antagonist ligands is evaluated by measurement of the decrease in variations, normally induced by CD40L, observed by preincubating the CDs in the presence of the antagonist molecules. The effect of ligands can also be tested (i) on the switching of classes of B lymphocytes, which can be mimicked in vitro by the activation of B cells of the tonsils by CD40 in the presence of cytokines, and (ii) on the differentiation of cytotoxic T lymphocytes which can be mimicked by a coincubation of dendritic cells activated by CD40 and precytotoxic T cells.

III—Tests of the Ligands in Models In Vivo:

The ligands L4 and L9 having been shown to be agonists, they represent interesting leads for testing the therapeutic effect of our molecules. The systemic lupus erythematosus is a systemic auto-immune disease in which the importance of the CD40-CD40L interaction is well documented. The treatment of lupic mice with agonist anti-CD40 antibodies greatly accelerates the lupus disease. In order to test the in vivo effect of the different ligands, we injected them into mice which spontaneously develop a lupus disease presenting symptoms like the human systemic lupus erythematosus. We studied the effect of the ligands on the development of the disease.

Operating Method

Preautoimmune MRL-$^{lpr}$ mice (Koopman et al., 1988) (aged 5 weeks) are injected by intravenous route with 100 µL per mouse of PBS containing or not containing 100 µg of ligand L4. The injection is repeated twice at a 2-week interval. The serum of these mice is regularly sampled by retro-orbital bleeding. The development of the lupus disease is monitored by a measurement of the proteinuria in the urine, of the presence of anti-DNA antibodies in the serum with an ELISA test and by the survival of the mice. These two markers are characteristic of the development of the lupus disease in MRL-$^{lpr}$ mice.

Results

The mice treated with the ligand L4 die significantly (p=0.0101) more quickly than the mice treated with PBS (FIG. 5A). This acceleration of mortality is accompanied by an earlier appearance of the anti-DNA in the serum (FIG. 5B) and of the proteinuria in the urine (FIG. 5C), showing that death is undoubtedly due to an acceleration of the lupus disease. These results clearly show that the ligand L4 has an agonist effect in vivo.

REFERENCES

Bjorck, P., Banchereau, J., Flores-Romo, L. (1997) CD40 ligation counteracts Fas-induced apoptosis of human dendritic cells, *Int Immunol.,* 9: 365-72, Buelens, C., Verhasselt, V., De Groote, D., Goldman, M., Willems, F. (1997) Human dendritic cell responses to lipopolysaccharide and CD40 ligation are differentially regulated by interleukin-10, *Eur J. Immunol.,* 27: 1848-52, Chaussabel, D., Jacobs, F., de Jonge, J., de Veerman, M., Carlier, Y., Thielemans, K., Goldman, M., Vray, B. (1999) CD40 ligation prevents *Trypanosoma cruzi* infection through interleukin-12 upregulation, *Infect Immun.,* 67: 1929-34, Diehl, L., den Boer, A. T., Schoenberger, S. P., van der Voort, E. I., Schumacher, T. N., Melief, C. J., Offring a, R., Toes, R. E. (1999) CD40 activation in vivo overcomes peptide-induced peripheral cytotoxic T-lymphocyte tolerance and augments anti-tumor vaccine efficacy, *Nat. Med.,* 5: 774-9, Howard, L. M., Miga, A. J., Vanderlugt, C. L., Dal Canto, M. C., Laman, J. D., Noelle, R. J., Miller, S. D. (1999) Mechanisms of immunotherapeutic intervention by anti-CD40L (CD154) antibody in an animal model of multiple sclerosis, *J Clin Invest.,* 103: 281-90, Kaiser, E. et coll. (1970) Anal. Biochem., 34, 595-598, Kikuchi, T., Moore, M. A., Crystal, R. G. (2000) Dendritic cells modified to express CD40 ligand elicit therapeutic immunity against preexisting murine tumors, *Blood.* 96: 91-9, Kirk, A. D., Burkly, L. C., Batty, D. S., Baumgartner, R. E., Berning, J. D., Buchanan, K., Fechner, J. H., Jr., Germond, R. L., Kampen, R. L., Patterson, N. B., Swanson, S. J., Tadaki, D. K., TenHoor, C. N., White, L., Knechtle, S. J., Harlan, D. M. (1999) Treatment with humanized monoclonal antibody against CD154 prevents acute renal allograft rejection in non-human primates, *Nat. Med.,* 5: 686-93, Koopman W. J. and Gay, S. (1988) The MRL-lpr/lpr mouse. A model for the study of rheumatoid arthritis. *Scand. J. Rheumatol.* 75, 284-289, Koppi, T. A., Tough-Bement, T., Lewinsohn, D. M., Lynch, D. H., Alderson, M. R. (1997) CD40 ligand inhibits Fas/CD95-mediated apoptosis of human blood-derived dendritic cells, *Eur J Immunol.,* 27: 3161-5, Locksley et al. (2001)*Cell,* 104, 487-501, Lode, H. N., Xiang, R., Pertl, U., Forster, E., Schoenberger, S. P., Gillies, S. D., Reisfeld, R. A. (2000) Melanoma immunotherapy by targeted IL-2 depends on CD4(+) T-cell help mediated by CD40/CD40L interaction, J Clin Invest., 105: 1623-30, Miga, A. J., Masters, S. R., Durell, B. G., Gonzalez, M., Jenkins, M. K., Maliszewski, C., Kikutani, H., Wade, W. F., Noelle, R. J. (2001) Dendritic cell longevity and T cell persistence is controlled by CD154-CD40 interactions, *Eur J Immunol.,* 31: 959-965, Schattner, E. J., Mascarenhas, J., Bishop, J., Yoo, D. H., Chadburn, A., Crow, M. K., Friedman, S. M. (1996) CD4$^+$ T-cell induction of Fas-mediated apoptosis in Burkitt's lymphoma B cells, *Blood,* 88: 1375-82, Sotomayor, E. M., Borrello, I., Tubb, E., Rattis, F. M., Bien, H., Lu, Z., Fein, S., Schoenberger, S., Levitsky, H. I. (1999) Conversion of tumor-specific CD4+ T-cell tolerance to T-cell priming through in vivo ligation of CD40. *Nat. Med.,* 5: 780-7, Tong, A. W., B. Seamour, J. Chen, D. Su, G. Ordonez, L. Frase, G. Netto, and M. J. Stone. 2000. CD40 ligand-induced apoptosis is Fas-independent in human multiple myeloma cells. *Leuk Lymphoma* 36:543-558.

The invention claimed is:

1. A multimeric molecule, corresponding to the following general formula:

$$A\text{-}X_n$$

wherein:
- n is equal to 3, 4, 5 or 6,
- A is a chemical moiety, functionalized by at least three amino functions or COOH functions or SH functions or S-Npys (S-nitro-pyridinesulphenyl) functions or S-Pys (S-pyridinesulphenyl) functions, and
- X represents a -D, —B-D, or —B(D)-D' group, in which:
  B is a spacer arm, and
  -D and -D' each represent a peptide corresponding to a sequence derived from a ligand, chosen from the residues forming the interface with the ligand receptor, said sequence capable of interacting with the receptor, said ligand being CD40L.

2. The molecule of claim 1, wherein -D and -D' each represent a peptide derived from the ligand of the human or murine CD40 receptor (CD40L), each said peptide belonging to the primary sequence of the CD40L and comprising between 3 and 10 amino acids.

3. The molecule of claim 1, wherein each peptide derived from the ligand of the human or murine CD40 receptor (CD40L) is chosen from the following:

Lys-Gly-Tyr (SEQ ID NO: 1),
Tyr-Gly-Lys (SEQ ID NO: 2),
Lys-Gly-Tyr-Tyr (SEQ ID NO: 3),
Tyr-Tyr-Gly-Lys (SEQ ID NO: 4),
Lys-Pro-Arg (SEQ ID NO: 5),
Arg-Phe-Glu-Arg-Ile-Leu-Leu-Arg (SEQ ID NO: 6),
Arg-Leu-Leu-Ile-Arg-Glu-Phe-Arg (SEQ ID NO: 7),
Arg-Phe-Glu-Arg-Ile (SEQ ID NO: 25),
Ile-Arg-Glu-Phe-Arg (SEQ ID NO: 9),

Arg-Ile-Leu-Leu-Arg (SEQ ID NO: 10),
Arg-Leu-Leu-Ile-Arg (SEQ ID NO: 11),
Cys-Gly-Gln-Gln-Ser-Ile (SEQ ID NO: 12),
Ile-Ser-Gln-Gln-Gly-Cys (SEQ ID NO: 26),
Gly-Ser-Glu-Arg-Ile-Leu-Leu-Lys (SEQ ID NO: 14),
Lys-Leu-Leu-Ile-Arg-Glu-Ser-Gly (SEQ ID NO: 15),
Gly-Ser-Glu-Arg-Ile (SEQ ID NO: 16),
Ile-Arg-Glu-Ser-Gly (SEQ ID NO: 17),
Arg-Ile-Leu-Leu-Lys (SEQ ID NO: 18),
Lys-Leu-Leu-Ile-Arg (SEQ ID NO: 19),
Cys-Glu-Gln-Gln-Ser-Val (SEQ ID NO: 20), or
Val-Ser-Gln-Gln-Glu-Cys (SEQ ID NO: 21),
or from hybrid peptides comprising at least two consecutive amino acids of two of the sequences defined above,
or from fragments of said peptides and hybrid peptides, the amino acids being equally able to be of L or D-configuration.

4. The molecule of claim 1, wherein A has a $C_3$ symmetry.

5. The molecule of claim 1, wherein:
either A is a branched radical with $C_3$ symmetry with the following general formula:

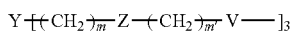

in which:

m and m' are integers comprised from 1 to 5,
V represents an —NH— or —CO— group forming an amide bond with X,
Z represents an oxygen atom or a CH2 group, and
Y represents either a nitrogen atom, or an R—C— group or an R—CONH—C— group, in which R can be an alkyl group with 1 to 10 carbon atoms, an alkenyl group with 1 to 10 carbon atoms, an alkynyl group with 1 to 10 carbon atoms, an aryl group with 5 to 12 carbon atoms, an aralkyl group with 5 to 14 carbon atoms or a heteroaryl group with 1 to 10 carbon atoms, said groups are capable of being non-substituted or substituted by 1 to 6 substituents chosen from the —COOH, —NH2, —CONH2 or alkoxy groups, or A is a cyclic C3 radical corresponding to one of the following general formulae:

Ia
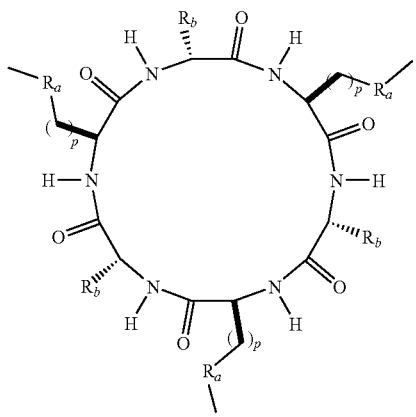

Ib
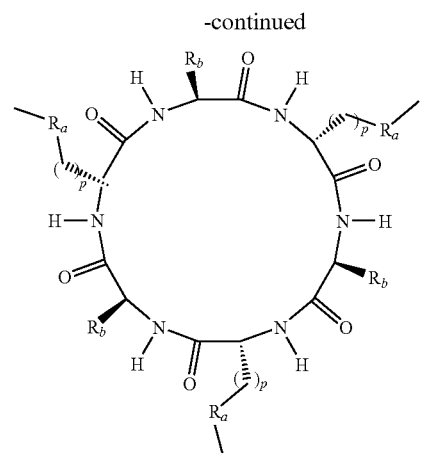

II
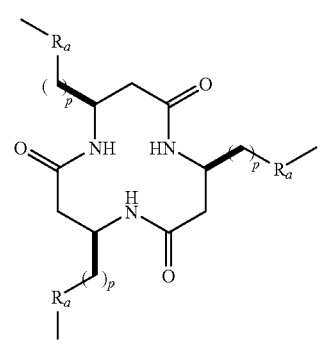

III
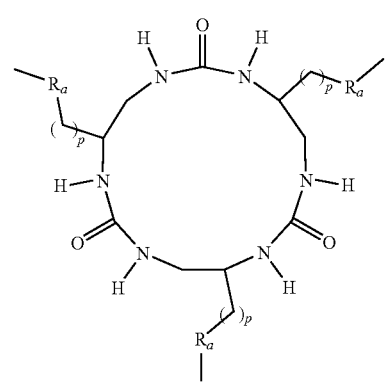

IV
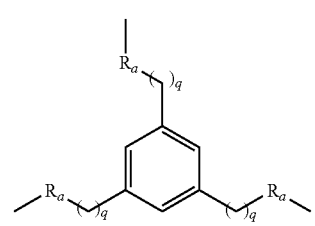

-continued

V

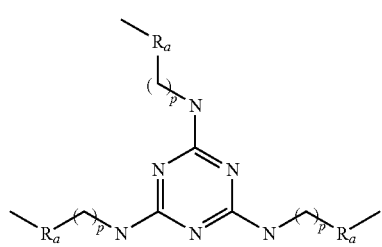

VI

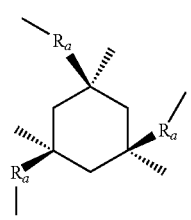

VIa

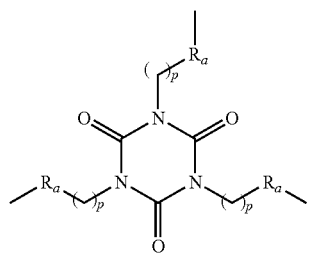

VIb

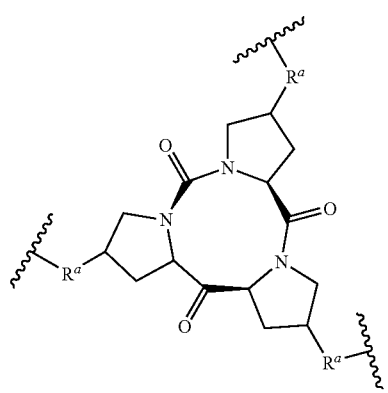

VIc

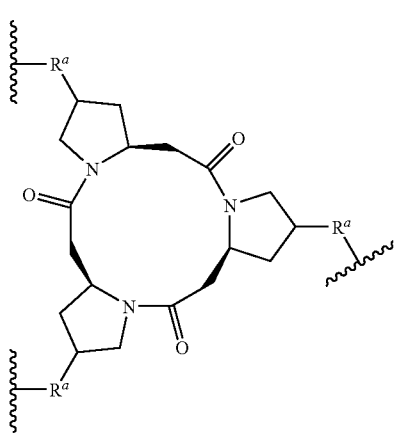

-continued

VId

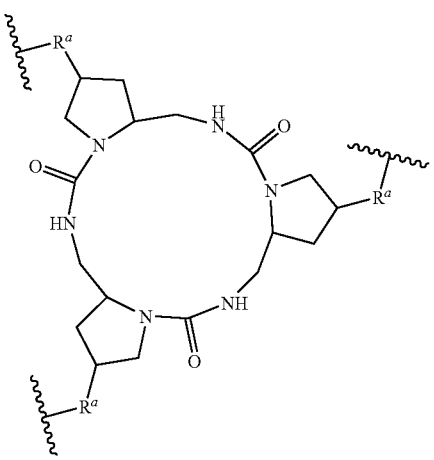

in which:

$R_a$ represents either an —NH— group or a —CO— group forming an amide bond with X, $R_b$ represents the side chain of a proteinogenic amino acid, p is an integer comprised from 1 to 4, and q is an integer comprised from 0 to 4, or A is a non-symmetrical branched radical corresponding to the following general formulae:

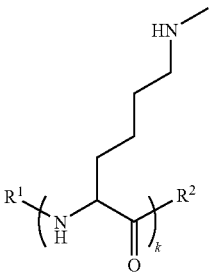

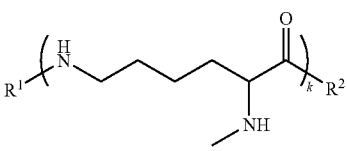

in which:

k represents 3, 4, 5 or 6, $R^1$ represents either a hydrogen atom, or an amino acid residue chosen from the proteinogenic amino acids, or an RCO—, ROCO— or RNHCO— group, R being as defined above, $R^2$ represents either an —NH$_2$ group, or an —NHR group, or an amino acid residue chosen from the proteinogenic amino acids, R being as defined above, and B corresponds to one of the following general formulae:

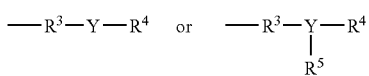

in which:
- Y represents a $C_1$-$C_{10}$ alkyl chain or an alkynyl or alkenyl or aryl or aralkyl or heteroaryl group,
- $R^3$ represents either an —NH— group when V or $R_a$ is a —CO— group, or a —CO— group when V or $R_a$ is an —NH— group,
- $R^4$ and $R^5$ represent independently of one another a —CO— group or an —NH— group, and
- -D and -D' are each a peptide as defined in claim 1.

6. The molecule of claim 1, wherein A corresponds to one of the following formulae:

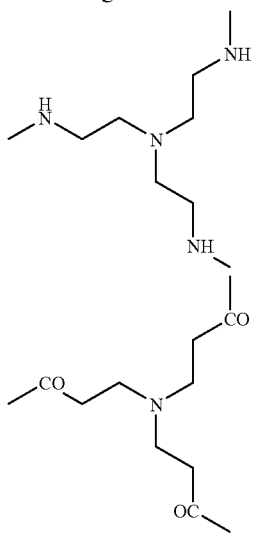

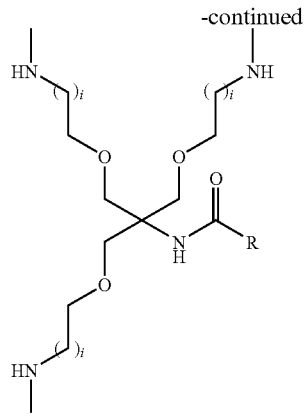

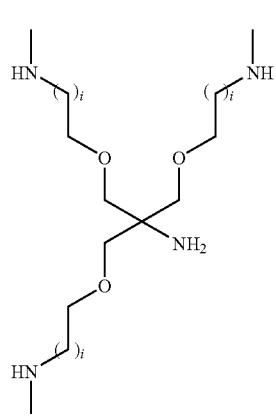

in which i represents an integer greater than or equal to 1.

7. The molecule of claim 1, of the following formula (peptide sequence KGYY disclosed as SEQ ID NO: 3):

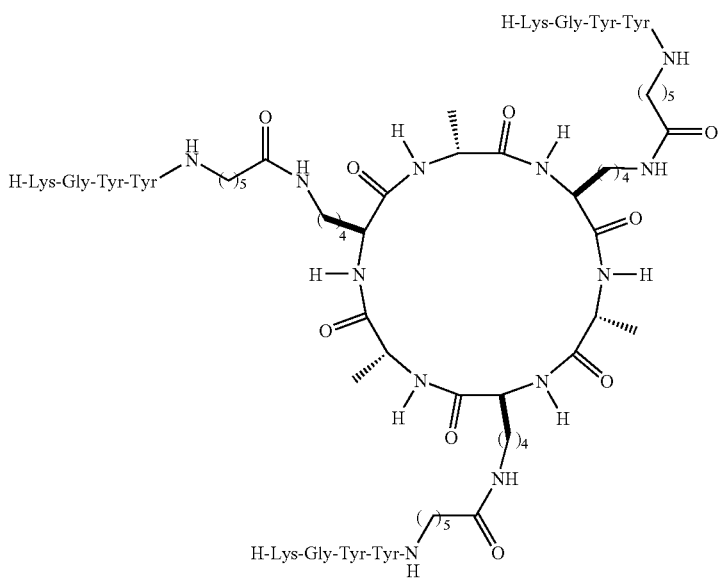

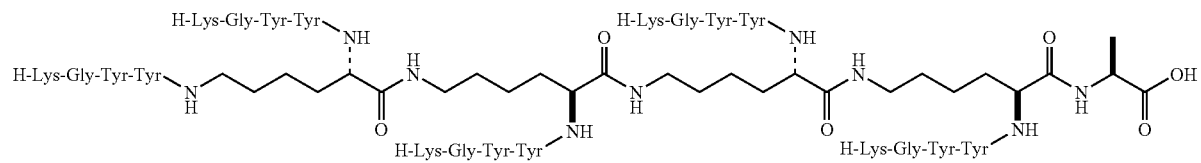
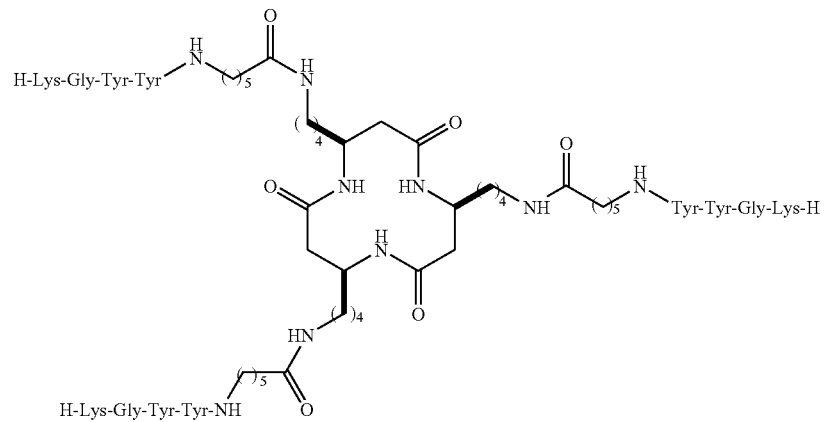
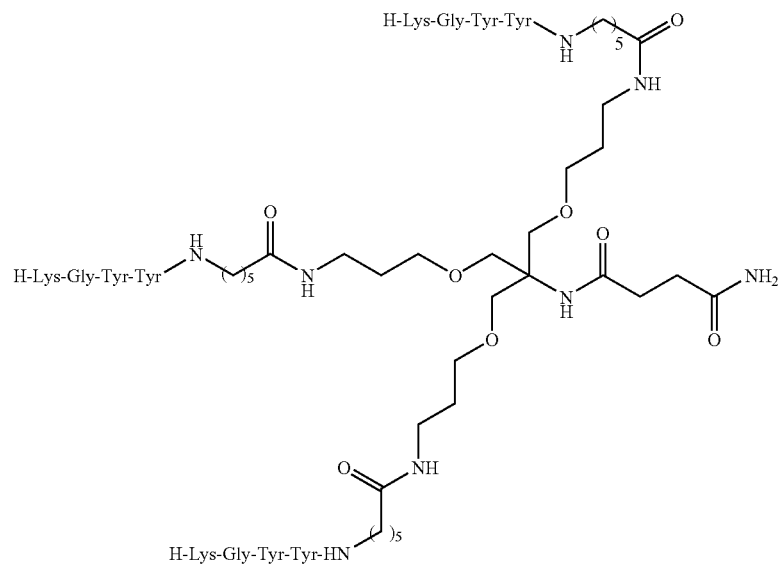

-continued
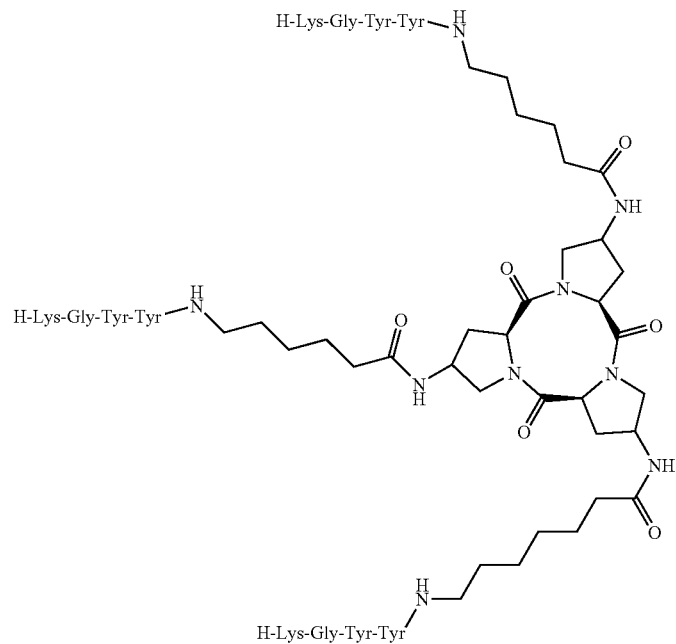
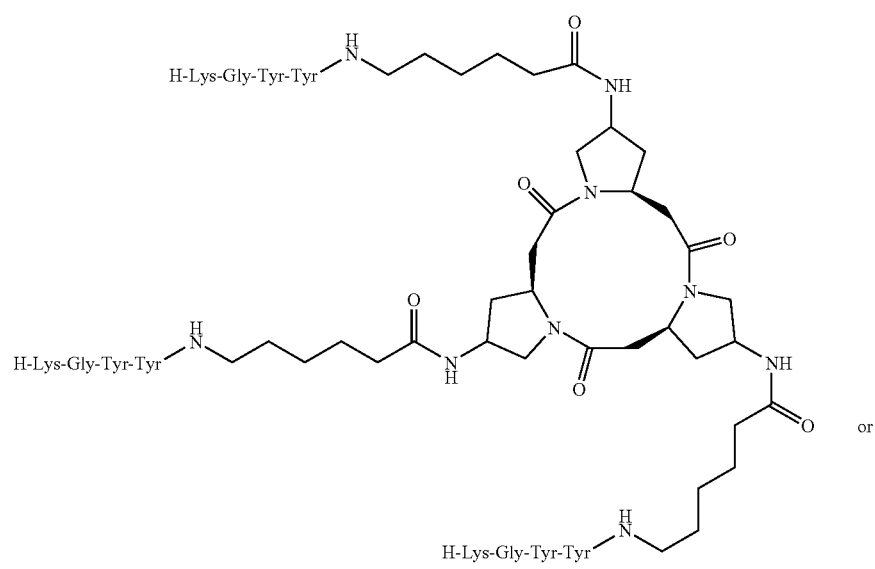
or

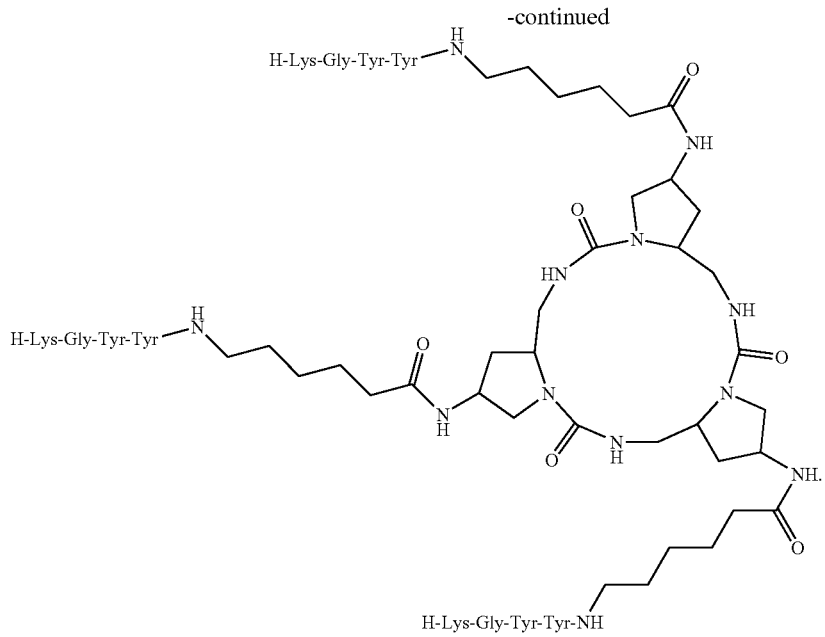

8. A pharmaceutical composition comprising, as active ingredient, a multimeric molecule according to claim 1, in combination with a pharmaceutically acceptable carrier.

9. A process for the preparation on a solid support of a multimeric molecule as defined in claim 5, in which A is a cyclic $C_3$ radical and corresponds to one of formulae Ia, Ib, II, VIb, VIc or VId, said process comprising:
forming a linear precursor of A comprising an amino acid sequence forming a growing peptide chain, synthesized by successive coupling cycles between residues of N-protected amino acids and the amine function of the growing peptide chain, and deprotection, wherein three of the amino acid residues comprise an amine-type $R_a$ group and the first amino acid residue is attached to a solid support,
cyclizing the protected linear precursor of A,
cleaving the protective groups, in order to release the protected amine functions,
coupling the three released amine functions with an N-protected spacer arm B,
deprotecting the spacer arm B and coupling the amine functions released from the spacer arm B, with a D peptide already formed or formed in situ by the sequential assembly of the amino acid residues corresponding to the D peptide, and
cleaving the molecule from the solid support, after deleting all the protective groups present on the functionalized side chains of the D peptide, in order to obtain the multimeric molecule.

10. A process for the preparation in solution of a multimeric molecule as defined in claim 5, in which A is a cyclic $C_3$ radical and corresponds to one of formulae Ia, Ib, II, VIb, VIc or VId, said process comprising:
forming a linear precursor of A comprising an amino acid sequence forming a growing peptide chain, synthesized by successive coupling cycles between N-protected amino acid residues and the amine function of the growing peptide chain, and deprotection, wherein three of the amino acid residues comprise an amine-type $R_a$ group
cyclizing the protected linear precursor of A,
cleaving the protective groups, in order to release the protected amine functions,
coupling the three released amine functions with a -D-B peptide corresponding to a spacer arm B linked to a protected D peptide,
of deprotecting the protective groups present on the D peptide, in order to obtain the multimeric molecule.

11. A process for the preparation of a multimeric molecule as defined in claim 5, in which A is a branched $C_3$ radical and corresponds to one of formulae IV, V, VI or VIa, said process comprising:
coupling the three amine functions of the radical A of formula IV, V, VI or VIa with a protected spacer arm B,
deprotecting the spacer arm B,
assembling the deprotected spacer arm B with protected amino acids involved in the constitution of a D peptide, by successive cycles of coupling, purification and deprotection of the amino acids,
deprotecting the last amino acid involved in the constitution of the D peptide, in order to obtain the multimeric molecule.

12. A process for the preparation on a solid support of a multimeric molecule as defined in claim 5, in which A is a non-symmetrical branched radical corresponding to one of formulae VII or VIII, said process comprising:
grafting a lysine onto a solid support, each of the two amino functions of the lysine, in positions α and ε, being protected by different and orthogonal protective groups,
extending the peptide chain formed from the lysine, to the desired length, with successive couplings and deprotections,
coupling the deprotected amino functions in position ε in the radical A of formula VII or in α position in the radical A of formula VIII, with a protected arm B,
assembling the deprotected spacer arm B with a D peptide already formed or formed in situ by the sequential assembly of the amino acid residues corresponding to the D peptide, and
cleaving the molecule thus obtained from the solid support, after deleting all the protective groups present on the functionalized side chains of the D peptide, in order to obtain the multimeric molecule.

13. The molecule of claim 1, wherein each peptide derived from the ligand of the human or murine CD40 receptor (CD40L) is chosen from the following:
Arg-Ile-Tyr-Tyr (SEQ ID NO: 22),
Arg-Ile-Tyr-Tyr-Gly-Lys (SEQ ID NO: 23),
or from fragments of said peptides,
the amino acids being equally able to be of L or D-configuration.

14. A method of treating lupus in a subject, comprising administering to the subject an effective amount of a multimeric molecule of claim 1.

15. A method of treating lymphoma in a subject, comprising administering to the subject an effective amount of a multimeric molecule of claim 1.

16. A method of treating parasitic infections in a subject, comprising administering to the subject an effective amount of a multimeric molecule of claim 1.

17. The method according to claim 16, wherein said parasitic infection is Chagas' disease.

* * * * *

SEQUENCE LISTING

<160> NUMBER OF SEQ ID NOS: 27

<210> SEQ ID NO 1
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Gly Tyr
 1

<210> SEQ ID NO 2
<211> LENGTH: 3

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Gly Lys
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Gly Tyr Tyr
  1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Tyr Gly Lys
  1

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Pro Arg
  1

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Phe Glu Arg Ile Leu Leu Arg
  1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Leu Leu Ile Arg Glu Phe Arg
```

-continued

```
          1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Arg Glu Arg Ile
 1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Arg Glu Phe Arg
 1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ile Leu Leu Arg
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Leu Leu Ile Arg
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Gly Gln Gln Ser Ile
 1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
```

-continued

```
       peptide

<400> SEQUENCE: 13

Ile Ser Gln Gln Glu Gly
 1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Ser Glu Arg Ile Leu Leu Lys
 1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Leu Leu Ile Arg Glu Ser Gly
 1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Ser Glu Arg Ile
 1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Arg Glu Ser Gly
 1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ile Leu Leu Lys
 1               5

<210> SEQ ID NO 19
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Leu Leu Ile Arg
  1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys Glu Gln Gln Ser Val
  1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Ser Gln Gln Glu Cys
  1               5

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ile Tyr Tyr
  1

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Ile Tyr Tyr Gly Lys
  1               5

<210> SEQ ID NO 24
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
```

-continued

```
<223> OTHER INFORMATION: PSI(CH2NH)Pro

<400> SEQUENCE: 24

Lys Xaa Arg
  1

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Phe Glu Arg Ile
  1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Ser Gln Gln Gly Cys
  1               5

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Boc)
<220> FEATURE:
<221> NAME/KEY: MOD_RES
<222> LOCATION: (3)..(4)
<223> OTHER INFORMATION: Tyr(tBu)

<400> SEQUENCE: 27

Xaa Gly Xaa Xaa
  1
```